(12) United States Patent
Grote

(10) Patent No.: US 11,191,304 B2
(45) Date of Patent: Dec. 7, 2021

(54) MULTI-ELEMENT VAPORIZER SYSTEM AND APPLICATION

(71) Applicant: Mark James Grote, River Forest, IL (US)

(72) Inventor: Mark James Grote, River Forest, IL (US)

( * ) Notice: Subject to any disclaimer, the term of this patent is extended or adjusted under 35 U.S.C. 154(b) by 0 days.

(21) Appl. No.: 17/325,979

(22) Filed: May 20, 2021

(65) Prior Publication Data
US 2021/0267282 A1    Sep. 2, 2021

Related U.S. Application Data

(63) Continuation-in-part of application No. 16/238,472, filed on Jan. 2, 2019.
(Continued)

(51) Int. Cl.
*A24F 40/60* (2020.01)
*H04L 29/08* (2006.01)
(Continued)

(52) U.S. Cl.
CPC .............. *A24F 40/60* (2020.01); *A24F 40/30* (2020.01); *A24F 40/42* (2020.01); *A24F 40/57* (2020.01);
(Continued)

(58) Field of Classification Search
CPC ....................................................... H05B 3/06
(Continued)

(56) References Cited

U.S. PATENT DOCUMENTS

| 8,820,330 B2 * | 9/2014 | Bellinger | A24F 40/50 |
| | | | 131/273 |
| 8,851,083 B2 * | 10/2014 | Oglesby | A24F 42/10 |
| | | | 131/271 |

(Continued)

FOREIGN PATENT DOCUMENTS

| EP | 3416507 B1 | 4/2020 |
| EP | 3422880 B1 | 4/2020 |

(Continued)

*Primary Examiner* — Nina Bhat
(74) *Attorney, Agent, or Firm* — Robert McConnell; McConnell Law Firm

(57) ABSTRACT

A portable vaporizer system that includes two or more individual heating elements controlled by a switching element. The switching element is either an analog control such as toggle switch or button or a digitally controlled with a microprocessor.

Each heating element may be individually contained within a variety of cavity types and designs. These cavities enclose both the heating element and the material to be vaporized. Cavities may be removable or permanently installed on the device. Removable cavities may include screw or plug-in attachment types. Permanently installed cavities may have a removable lid for access to the interior of the cavity. Configurations of heating elements and cavities from two to twelve are shown.

Digitally controlled switching elements can be controlled from a native application installed on the vaporizer device or on a mobile computing device. The digital control applications may include a user profile, manual device controls, access to a remote blend database, eCommerce functions, social media integration and a user calendar. Native applications on a portable vaporizer device may be controlled by a digital touch screen and be connected to other devices by communication means such as Bluetooth or WiFI.

20 Claims, 29 Drawing Sheets

Related U.S. Application Data

(60) Provisional application No. 62/780,755, filed on Dec. 17, 2018, provisional application No. 62/654,187, filed on Apr. 6, 2018.

(51) Int. Cl.
*A61M 11/00* (2006.01)
*A24F 40/57* (2020.01)
*A24F 40/65* (2020.01)
*A24F 40/42* (2020.01)
*A24F 40/30* (2020.01)
*A61M 15/00* (2006.01)

(52) U.S. Cl.
CPC ............ *A24F 40/65* (2020.01); *A61M 11/00* (2013.01); *A61M 15/0001* (2014.02); *H04L 67/12* (2013.01)

(58) Field of Classification Search
USPC ............. 131/194; 700/300; 128/202.21, 203
See application file for complete search history.

(56) References Cited

U.S. PATENT DOCUMENTS

| | | | | |
|---|---|---|---|---|
| 8,955,522 | B1* | 2/2015 | Bowen | A24F 40/42 |
| | | | | 131/270 |
| 9,408,416 | B2* | 8/2016 | Monsees | A24F 1/32 |
| 9,538,783 | B2* | 1/2017 | Xiang | A24F 40/95 |
| 9,839,236 | B2 | 12/2017 | Liu | |
| 9,888,723 | B2 | 2/2018 | Cameron et al. | |
| 9,936,738 | B2* | 4/2018 | Cameron | A24F 40/60 |
| 9,999,250 | B2 | 6/2018 | Minskoff et al. | |
| 10,004,271 | B2 | 6/2018 | Li et al. | |
| 10,039,327 | B2* | 8/2018 | Cameron | A24F 1/30 |
| 10,058,128 | B2* | 8/2018 | Cameron | H05B 3/12 |
| 10,091,839 | B2 | 10/2018 | Murison et al. | |
| 10,117,462 | B2 | 11/2018 | Johnson et al. | |
| 10,285,449 | B2 | 5/2019 | Murison et al. | |
| 10,346,153 | B2* | 7/2019 | Qiu | A24F 40/60 |
| 10,412,997 | B2 | 9/2019 | Cameron et al. | |
| 10,477,900 | B2 | 11/2019 | Hopps | |
| 10,201,181 | B2 | 12/2019 | Murison et al. | |
| 10,609,962 | B2 | 4/2020 | Zhu | |
| 10,925,319 | B2 | 2/2021 | Fornarelli | |
| 11,075,995 | B2* | 7/2021 | Woodbine | A24F 40/50 |
| 2011/0126848 | A1* | 6/2011 | Zuber | A24F 40/46 |
| | | | | 131/329 |
| 2014/0123989 | A1 | 5/2014 | LaMothe | |
| 2014/0261488 | A1 | 9/2014 | Tucker | |
| 2015/0080053 | A1* | 3/2015 | Ciccarello | H04M 1/21 |
| | | | | 455/557 |
| 2015/0181945 | A1* | 7/2015 | Tremblay | A24F 40/53 |
| | | | | 131/328 |
| 2016/0106936 | A1* | 4/2016 | Kimmel | A24F 40/51 |
| | | | | 128/202.21 |
| 2016/0331023 | A1 | 11/2016 | Cameron | |
| 2016/0338407 | A1 | 11/2016 | Kerdemelidis | |
| 2016/0353800 | A1 | 12/2016 | Di Carlo | |
| 2017/0042230 | A1* | 2/2017 | Cameron | A24F 40/60 |
| 2017/0042231 | A1 | 2/2017 | Cameron | |
| 2017/0045994 | A1 | 2/2017 | Murison et al. | |
| 2017/0135407 | A1* | 5/2017 | Cameron | G10L 17/00 |
| 2017/0181467 | A1 | 6/2017 | Cameron | |
| 2017/0182267 | A1 | 6/2017 | Cameron | |
| 2017/0332702 | A1* | 11/2017 | Cameron | A24B 15/167 |
| 2019/0217028 | A1* | 7/2019 | Nakano | A61M 11/041 |
| 2019/0281898 | A1 | 9/2019 | Hopps | |
| 2019/0307170 | A1 | 10/2019 | Zarifian et al. | |
| 2019/0369127 | A1 | 12/2019 | Fu et al. | |
| 2020/0022416 | A1 | 1/2020 | Alarcon | |
| 2020/0205478 | A1 | 7/2020 | Dick et al. | |
| 2020/0221778 | A1 | 7/2020 | Trecieski | |
| 2020/0359698 | A1 | 11/2020 | Lim et al. | |
| 2021/0023316 | A1 | 1/2021 | Schorr et al. | |

FOREIGN PATENT DOCUMENTS

| | | |
|---|---|---|
| WO | WO2019215213 | 11/2019 |
| WO | WO2019215213 A1 | 11/2019 |

* cited by examiner

MULTI-ELEMENT VAPORIZER SYSTEM AND APPLICATION

PRIORITY

This application is a continuation-in-part of application Ser. No. 16/238,472 the disclosure of which is incorporated by reference.

FIELD OF THE INVENTION

The present invention relates to the field of devices for vaporizing, smoking, burning or otherwise heating materials that humans inhale for various different mood effects such as inhalable *Cannabis*, tobacco, and e-cig substances in the form of fluids, oils, juices, waxes, dabs, shatters, distillates, flowers, hashes, tobacco and/or plant matter. As directly smoking various materials (cigarettes, tobacco, *Cannabis* or clove) has potential ill health effects, vaporization is often safer from a health perspective, provides output that is less troublesome that tobacco or *Cannabis* smoke and allows much greater control over the timing and temperature of vaporization. The present invention further allows the user to have multiple materials in their vaporizer device, for different mood effects, without reloading the device after each inhale.

Additionally, with the legalization of *Cannabis* in many states, consumers have displayed great interest in different methods to ingest vaporized *Cannabis*. Vaporization devices are very popular and allow vaporization of various forms of *Cannabis* plant such as dried *Cannabis* flowers, concentrates, oils, fluids manufactured for vaporization (vape juice, e-juice, etc.), shatters and dabs. There are many names for these products, but at the core they provide the same basic operative means: heat is applied to the material to be vaporized, a vapor or smoke is formed and the user inhales the vapor or smoke from the vaporizer device. The vaporizer devices come in many forms such as pens, pods and boxes with a variety of different cartridges, but they generally have a single heating element.

BACKGROUND OF THE INVENTION

Current vaporizer devices are often portable, handheld and battery powered but larger devices that plug into a wall socket are known in the art. The portable vaporizers often come in a variety of shapes, including pen shaped devices, rectangular shaped devices and others. These devices often use interchangeable cartridges some threaded to be screwed on and off, some that plug in and out, some that are pods and other varieties. A variety of control systems exist for the devices but they often have one heating element and allow the vaporization of one material at a time.

BACKGROUND ART

The prior art includes many configurations of single heating element vaporizers in terms of shape of the device, type of cartridge and cartridge connections. The prior art also includes vaporizers with more than one heating element, but none that allow individual control of each heating element.

Background art also includes more basic methods of smoking or vaporizing materials including pre-rolled cigarettes, hand-rolled cigarettes, pipes, water filtration devices and other various mechanisms for vaporization.

Regardless of the form of vaporization, the prior art is focused generally on the consumption of one material at a time in a vaporizer device.

OBJECTS OF THE INVENTION

It is an object of the invention to provide a vaporizer system for inhaling vaporized materials such as *Cannabis*, tobacco, and e-cig substances in the form of fluids, oils, juices, waxes, dabs, shatters, distillates, flowers, hashes, tobacco and/or plant matter.

It is an object of the invention to provide a vaporizer system with multiple heating elements for vaporizing two or more materials for vaporization.

It is an object of the invention to provide a multi-heating element vaporizer system with two or more cavities enclosing heating elements and material for vaporization.

It is an object of the invention to provide a multi-heating element vaporizer system with two or more removable cavities enclosing heating elements and material for vaporization.

It is an object of the invention to provide a multi-heating element vaporizer system with a switching element that controls activation, duration of activation and temperature of two or more heating elements.

It is an object of the invention to provide a multi-heating element vaporizer system where the switching element is a toggle switch.

It is an object of the invention to provide a multi-heating element vaporizer system where the switching element is a button.

It is an object of the invention to provide a multi-heating element vaporizer system where the switching element is digitally controlled by a computer.

It is an object of the invention to provide a multi-heating element vaporizer system where the digital control system is in the form of a mobile application installed on a mobile computing device.

It is an object of the invention to provide a multi-heating element vaporizer system where the digital control system includes communication means to communicate with a portable vaporizer.

It is an object of the invention to provide a multi-heating element vaporizer system where the digital control system includes a user interface.

It is an object of the invention to provide a multi-heating element vaporizer system where the digital control system includes a user profile.

It is an object of the invention to provide a multi-heating element vaporizer system where the digital control system includes manual device controls.

It is an object of the invention to provide a multi-heating element vaporizer system where the digital control system includes a user calendar.

It is an object of the invention to provide a multi-heating element vaporizer system where the digital control system includes eCommerce functions.

It is an object of the invention to provide a multi-heating element vaporizer system where the digital control system includes social media integrations.

It is an object of the invention to provide a multi-heating element vaporizer system where the digital control system includes access to a blend database.

It is an object of the invention to provide a multi-heating element vaporizer system where the digital control system is in the form of a native application installed on the portable vaporizer device.

It is an object of the invention to provide a multi-heating element vaporizer system with a digital touch screen.

It is an object of the invention to provide a multi-heating element portable vaporizer system that includes communications means to connect to a computer or mobile device.

It is an object of the invention to provide a multi-heating element portable vaporizer system that includes a microprocessor, memory and a digital touch screen controller.

It is an object of the invention to provide a multi-heating element portable vaporizer system that includes a variety of cavity shapes and sizes.

It is an object of the invention to provide a multi-heating element portable vaporizer system that includes a variety of cavity attachment and detachment types.

SUMMARY OF THE INVENTION

The present invention is a portable vaporizer system that includes two or more individual heating elements that can be controlled by a switching element. The switching element can be in the form of an analog control such as toggle switch or button or a digitally controlled with a microprocessor.

Each heating element may be individually contained within a variety of cavity types and designs. These cavities enclose both the heating element and the material to be vaporized. Cavities may be removable or permanently installed on the device. Removable cavities may include screw or plug-in attachment types. Permanently installed cavities may have a removable lid for access to the interior of the cavity. The preferred embodiment shows a configurations of heating elements and cavities from two to twelve but any number of heating elements is anticipated.

Digitally controlled switching elements can be controlled from a native application installed on the vaporizer device or on a mobile computing device. The digital control applications may include a user profile, manual device controls, access to a remote blend database, eCommerce functions, social media integration and a user calendar. Native applications on a portable vaporizer device may be controlled by a digital touch screen and be connected to other devices by communication means such as Bluetooth or WiFI.

DETAILED DESCRIPTION OF THE INVENTION

The following detailed description outlines the preferred embodiment of the claimed invention. There may be many other configurations that comport with the attached claim language and this description is in no way limiting to the scope of the invention.

The present invention relates to devices for vaporizing, heating, burning, smoking or otherwise applying heat to a material suitable for vaporization such as tobacco, *Cannabis*, vaporizer fluid comprised of nicotine, *Cannabis* (containing both THC and CBD), concentrates made from various materials such as tobacco or *Cannabis* and any other material that when heated creates a vapor or smoke suitable for human inhalation. The disclosed device allows the user to simultaneously consume two or more materials suitable for vaporization at one time, while controlling the amount of each material that is consumed. The devices disclosed include two or more heating elements controlled by a switching element for controlling the intensity and duration of the heat applied to each material so that the user can control the mix of the materials. This controllable mix of materials heated by the heating elements allows the user to manage the effect of the materials for various desired effects. In addition to devices containing multiple heating elements, the invention discloses a variety of types of switching elements and material containers. Lastly the preferred embodiment includes manual switching elements using switches or buttons as well as computer controlled switching elements controlled by microprocessors or mobile applications on a mobile smart phone.

Figure 1:
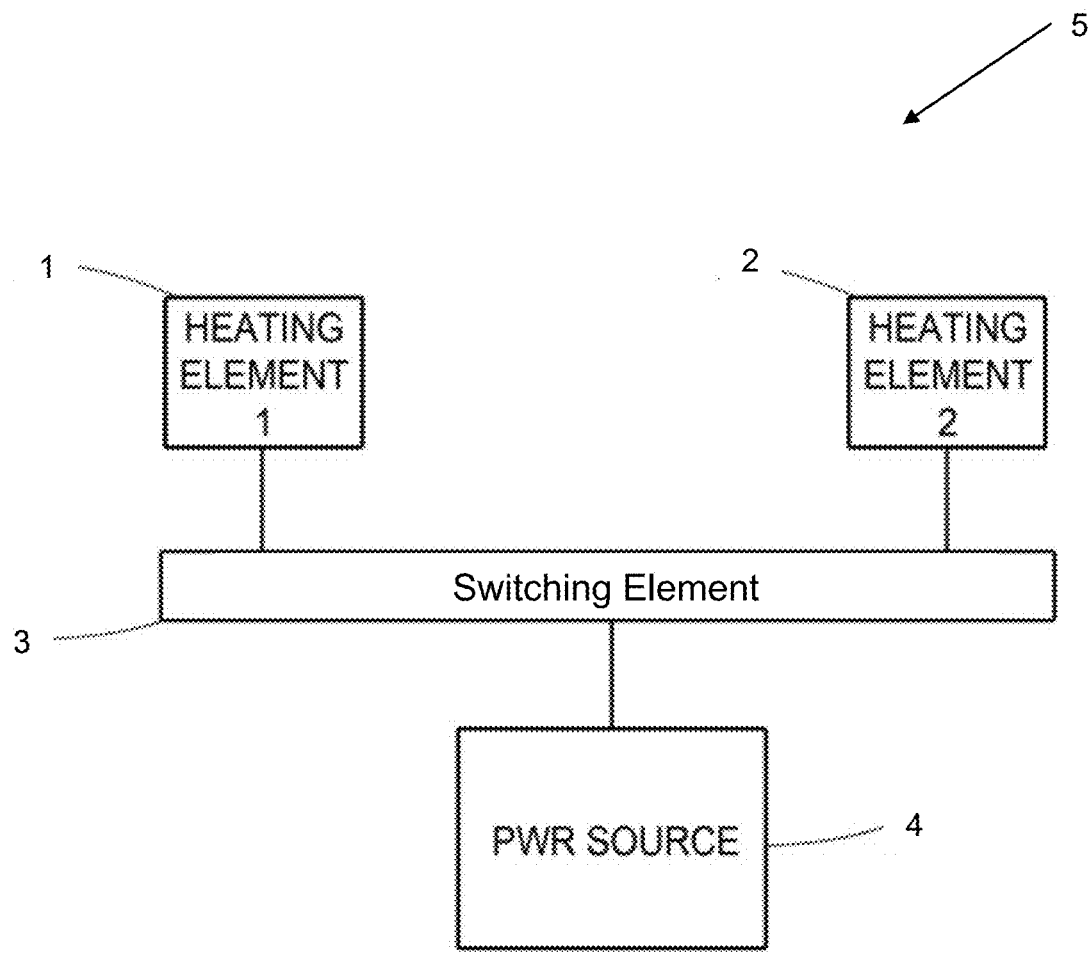
FIG. 1 shows a block diagram of the present invention with two heating elements, a switching element and a power source.

FIG. 1 shows a simple version of multi-element vaporizer system 5 comprising a first heating element 1, a second heating element 2, switching element 3 and power source 4. First heating element 1 and second heating element 2 are matched electrical heating elements well known in the vaporizer art. These heating elements generate heat by passing electrical current through a resistance element. When the resistance element slows the flow of current through it, heat is generated as a by-product. In the vaporizer world, these resistance elements are generally manufactured in three types of materials, metal, ceramic, glass and quartz, each with its own advantages and disadvantages. The heating elements of the claimed invention can be manufactured in any one of these three materials but also in any other suitable material for the application. Additionally, these heating elements generally use two types of heating: conduction and convection. Conduction applies heat directly via the heating element to the material to be vaporized and convention heats air with the heating element (separately from the material to be vaporized) and then passes the heated air over the material, thus vaporizing it. While these two methods are well known in the art, any other suitable heating method can be utilized with the claimed invention.

Switching element 3 controls the electrical voltage and current applied to each of the heating elements. Switching element 3 comes in two general types: analog and digital. Simple analog switching elements 3 use switches to manually turn each heating element on and off. Such switches include toggle switches and buttons, but other types of analog switches are anticipated. More complex analog switching elements may include rheostat type switches that enable infinitely adjustable current (and thus heat produced) for each heating element. This adjustability allows the user to tailor the amount of each material that is vaporized at a given time, in proportion to the other, for tailored impact of the material. An additional analog switching element is a timer for each heating element. This could be combined with either type of switch disclosed above to provide a more precise heating time for each element. These analog switching elements 3 are constructed of electrical components well known in the art such as resistors, capacitors, switches and adjustable resistance rheostat switches and analog timers. While the above described analog switching elements 3 are described in conjunction with the preferred embodiment, any other analog switching element 3 that controls the activation, intensity and duration of heat for any of the heating elements is anticipated by the claims of the invention.

Digital switching elements 3 utilize digital elements to more accurately control the activation, intensity and duration of the heat applied to the material to be vaporized. These digital elements are well known in the art and comprise microcontrollers and/or simple microprocessors that digital output signals to digitally controlled heating elements. Digital elements such as these include outputs that are described in "bits." Each one bit output has two positions, 0 (zero, voltage off) or 1 (one, voltage on). Various combinations of digital output bits can control various devices, including the heating elements of the present invention. Additionally, these digital elements easily connect to other digital elements such as smart phones, Bluetooth communication links and flat display screen (LCD, OLED and others) technologies.

The digital switching elements 3 can provide a nearly infinite range of output activation, intensity and timing for many heating elements. Specifically, such a switching element 3 could include two outputs, the first controlling power to heating element 1 and heating element 2. This power signal could be as simple as a one bit output that indicates heating element "on" when a digital 1 (one, or positive voltage) is output or heating element "off" when a digital 0 (zero, zero voltage) is output. Microcontroller/processors well known in the art utilize an internal clock signal that switches on (digital 1/voltage on) and off (digital 0/voltage off) at a set frequency, or rate at which the clock changes from zero to one over a given time frame, generally measured in hertz (HZ) or cycles per second. This internal clock signal can be used create digital timer circuitry that can control the duration of the on or off signal.

The second output utilized to control the heating element is a multi-bit (8 or more) intensity output that outputs a signal to indicate various levels of heating intensity for the heating device. For example, an 8-bit intensity output has up to 256 combinations of output bits to control the intensity of the heating element. Each of these 256 combinations indicate an intensity/heating level of each heating element to provide a vaporization characteristics for each type of material to be vaporized. In addition, these digital switching elements 3 can create heating patterns that provide desired user effects from each of the materials to be vaporized. Patterns could be turning heating element 1 on twice in rapid succession followed by heating element 3 three times in rapid succession. The combinations are infinite for such devices.

Power source 4 provides electrical energy for the multi-element vaporizer. This power can be 120/220 Hz AC power from a terrestrial plug in outlet or provided by various battery technologies well known in the art such as alkaline, nickel-cadmium, nickel metal hydride and lithium ion. While these power sources are discussed in the preferred embodiment, any suitable power source can be utilized.

Figure 2:
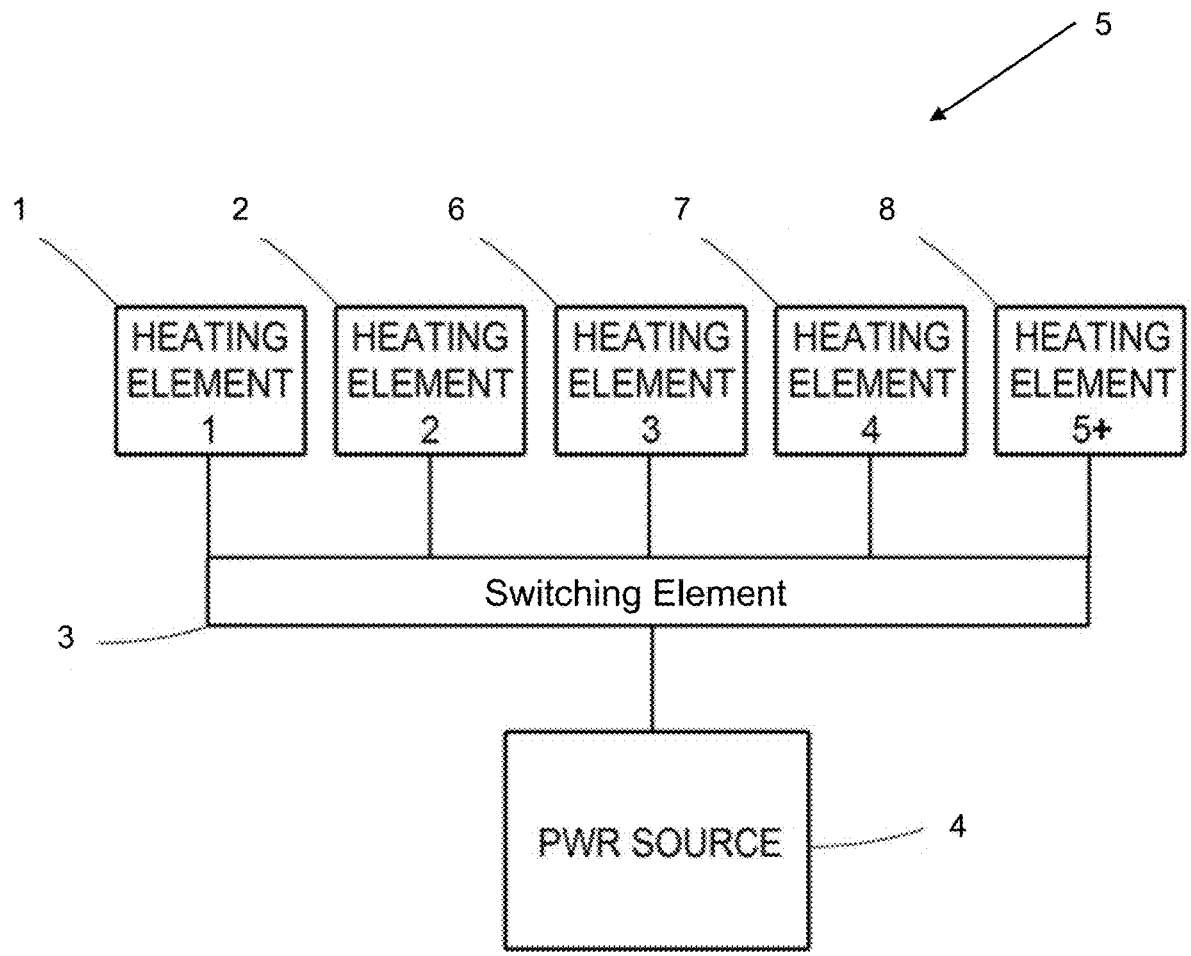
FIG. 2 shows a block diagram of the present invention with five heating elements, a switching element and a power source.

FIG. 2 shows a view of the multi-element vaporizer system 5 with five heating elements, specifically heating element 1, heating element 2, heating element 6, heating element 7 and heating element 8. This configuration shows that the present device can be used with any combination of number of heating elements for a variety of configurability options for the device. Switching element 3 and power source 4 are the same as described in FIG. 1.

Figure 3:
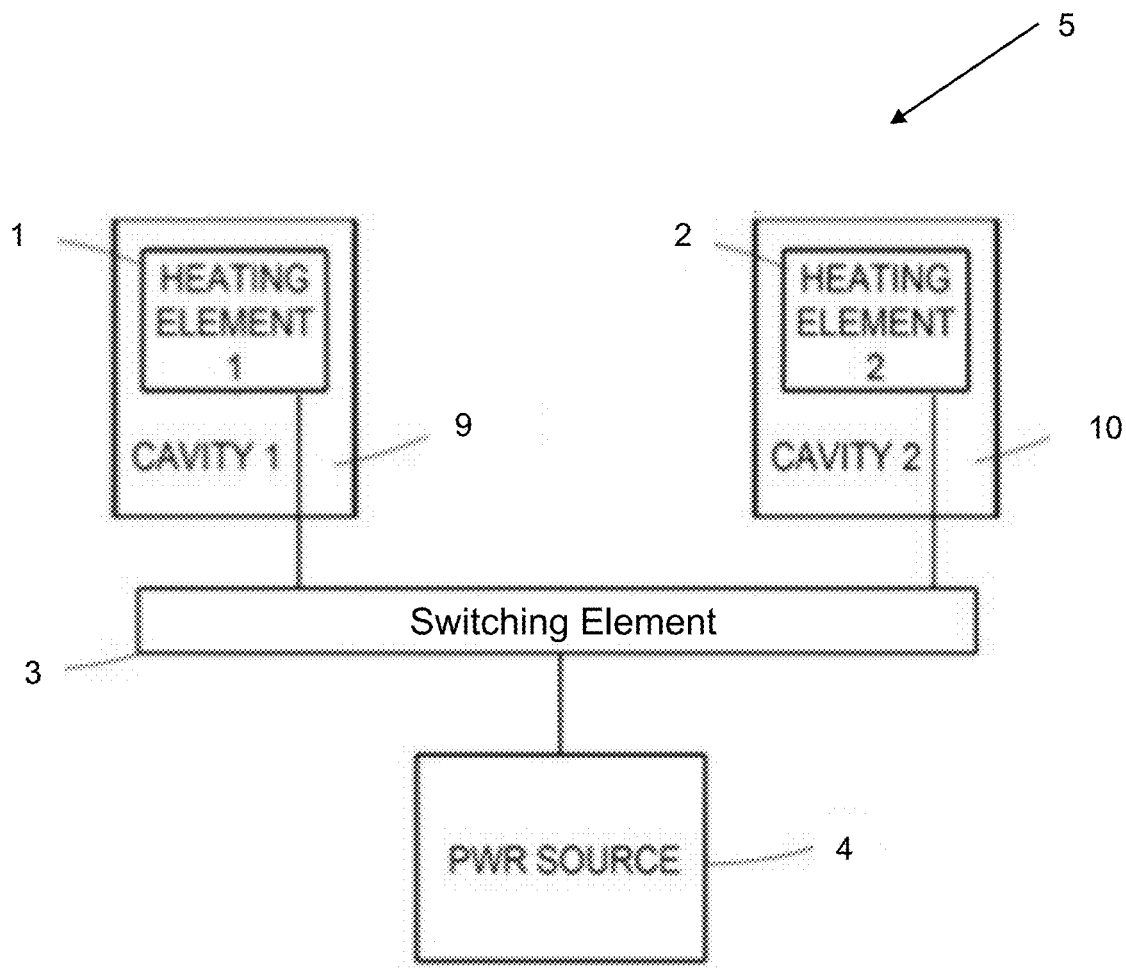
FIG. 3 shows a block diagram of the present invention with two heating elements, two cavities, a switching element and a power source.

FIG. 3 shows the multi-element vaporizer system 5 with two heating elements and a cavity surrounding each heating element. For example, heating element 1 is surrounded by first cavity 9. Cavity 9 holds the material that is to be vaporized by heating element 1. Cavity 9 is meant to broadly be defined as any enclosure that contains a material to be vaporized and allows it to come in contact with the heating element utilizing conduction, convection or any other heat application type known in the art. Cavity 9 and cavity 10 can be a cartridge or a pod with various different connection types to the device such as threads or other attachment means. Examples of various cavity designs suitable for use with the present invention will be shown and discussed in later figures. Switching element 3 and power source 4 are similar to those described in FIG. 1.

Figure 4:
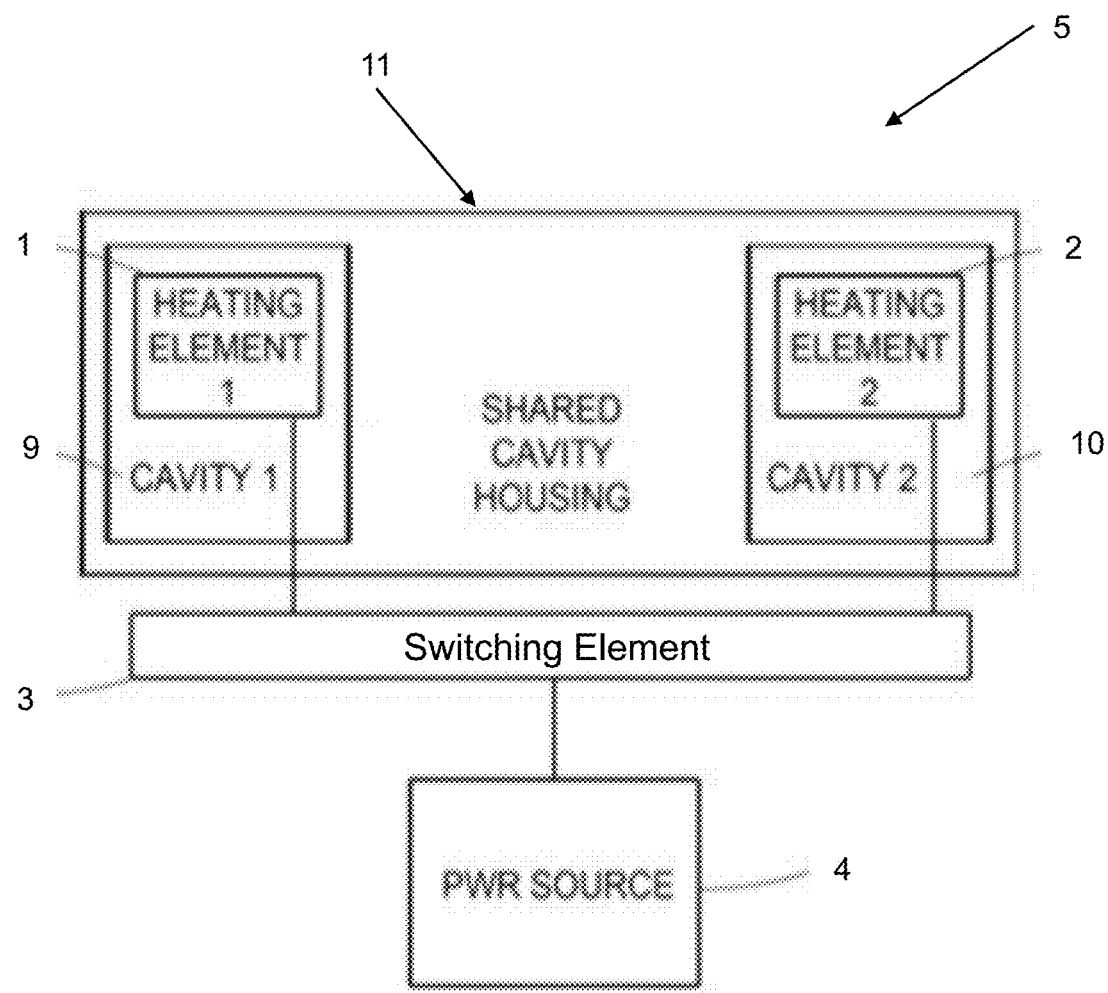
FIG. 4 shows a block diagram of the present invention with two heating elements, two cavities, a shared cavity housing, a switching element and a power source.

FIG. 4 shows the multi-element vaporizer system 5 with a shared cavity housing 11 that encloses both first cavity 8 and second cavity 10. This allows multiple types of material to be vaporized to be enclosed in separate cavities with separate heating elements but to be enclosed in a single housing for the user's convenience. Additional variations of this housing will be discussed relative to later figures. Power source 4, switching element 3 and heating elements 1 and 2 operate in the same manner as discussed prior.

Figure 5:
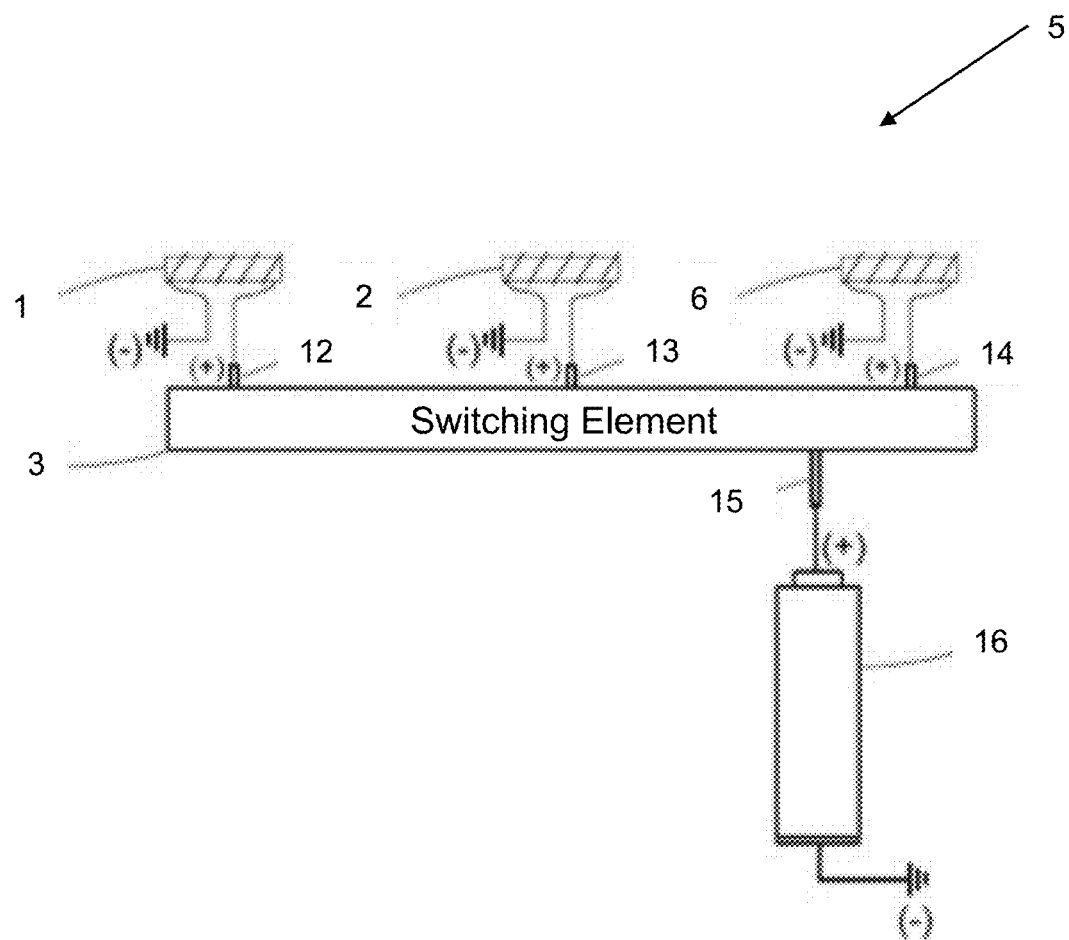
FIG. 5 shows a block diagram of the present invention with three heating elements, a switching element and a battery power source.

FIG. 5 displays a configuration of multi-element vaporizer system 5 with three heating elements and powered by a battery 16. In this configuration, switching element 3 is of the analog variety described above and has 3 positive electrodes with first positive electrode 12 connected to the positive electrode of first heating element 1, second positive electrode 13 connected to the positive electrode of second heating element 2 and third positive electrode 14 connected to the positive electrode of third heating element 6. Each positive electrode of switching element 3 controls the activation, duration and intensity of each connected heating element. Each heating element is also connected to ground as shown in the figure. Battery 16 is connected to positive power electrode 15 of switching element 3 as well as ground. Battery 16 could be a battery of any voltage or type as known in the art such as alkaline, nickel cadmium, nickel metal hydride or lithium ion.

Figure 6:
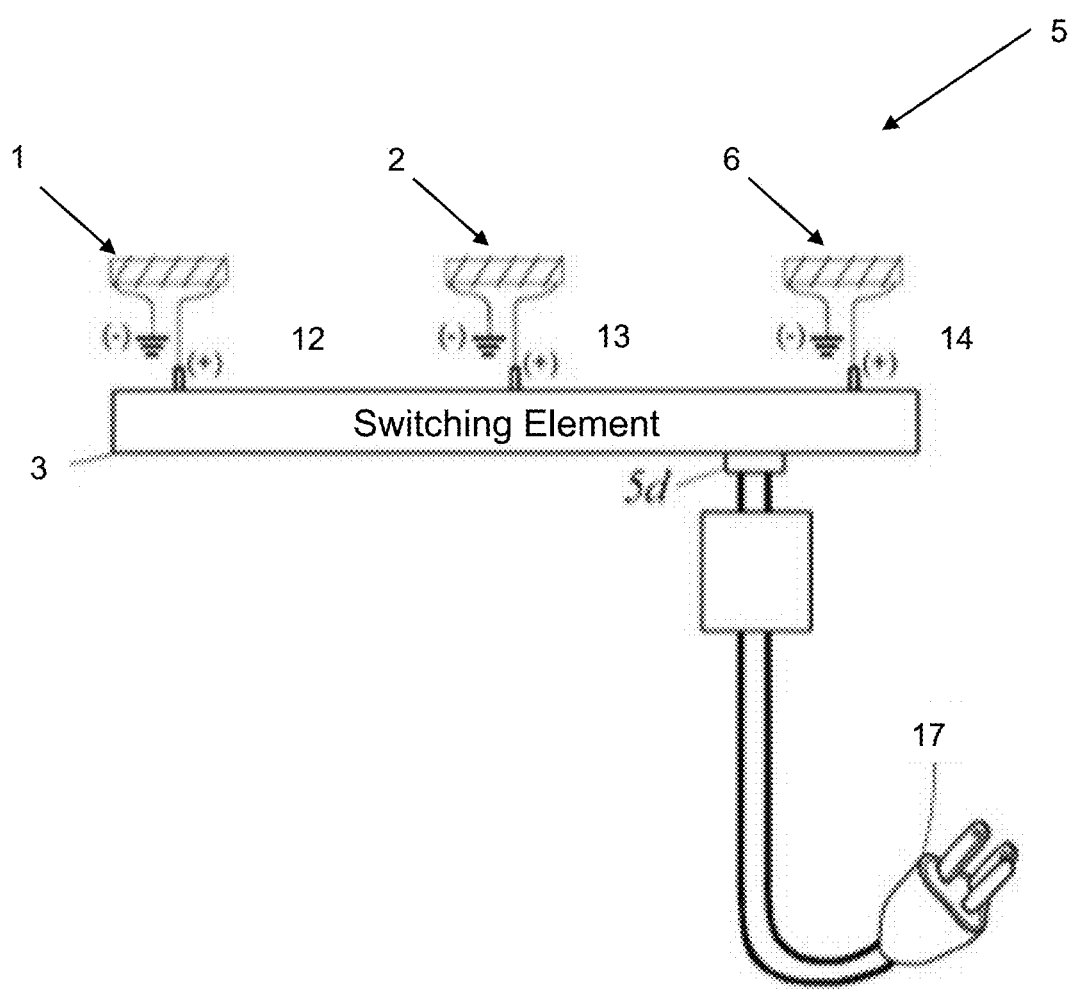
FIG. 6 shows a block diagram of the present invention with three heating elements, a switching element and an AC power source.

FIG. 6 displays an alternate configuration of the multi-element vaporizer system 5 with three heating elements and powered by a connection to AC power provided by a wall socket. As in FIG. 5, switching element 3 is of the analog variety described above and has 3 positive electrodes with first positive electrode 12 connected to the positive electrode of first heating element 1, second positive electrode 13 connected to the positive electrode of second heating element 2 and third positive electrode 14 connected to the positive electrode of third heating element 6. Each positive electrode of switching element 3 controls the activation, duration and intensity of each connected heating element. Each heating element is also connected to ground as show in the figure. Power source 17 is of the AC type connected to a wall socket in a voltage well known in the art, either 110V or 220V.

Figure 7:
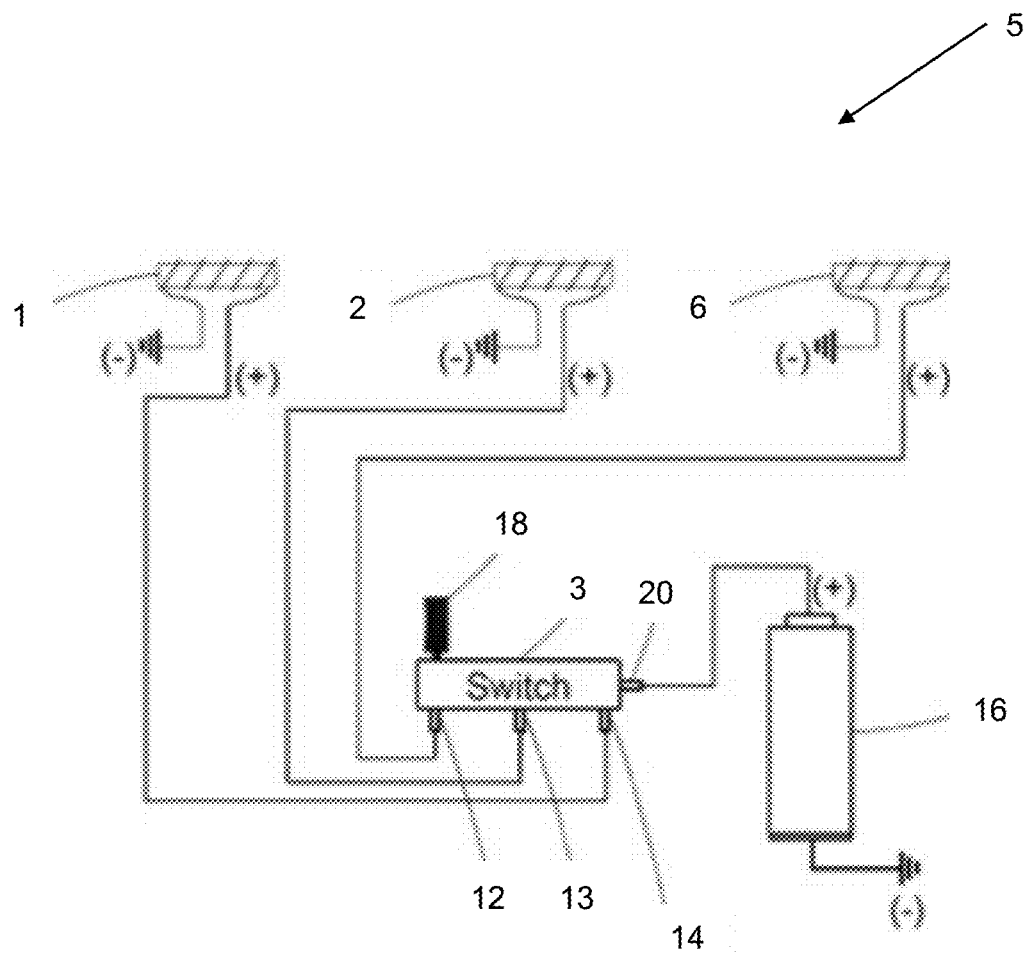
FIG. 7 shows a block diagram of the present invention with three heating elements, a toggle switching element and a battery power source.

FIG. 7 displays an alternate configuration of the multi-element vaporizer system 5 with three heating elements, powered by a battery and including a three way switch for switching element 3. Switching element 3 is of the analog variety described above, in this case including a three position switch, and has 3 positive electrodes with first positive electrode 12 connected to the positive electrode of third heating element 6, second positive electrode 13 connected to the positive electrode of second heating element 2 and third positive electrode 14 connected to the positive electrode of first heating element 1. Switch 18 controls which of the heating elements are activated by switching element 3. When switch 18 is in the first position (left most position), third heating element 6 receives electrical power and is activated. When switch 18 is in the second position (center position), second heating element 2 receives electrical power and is activated. When switch 18 is in the third position (right most position), first heating element 1 receives electrical power and is activated. Each heating element is also connected to ground as show in the figure. Battery 16 is connected to power electrode 20 could be a battery of any voltage or type as known in the art such as alkaline, nickel cadmium, nickel metal hydride or lithium ion.

Figure 8:
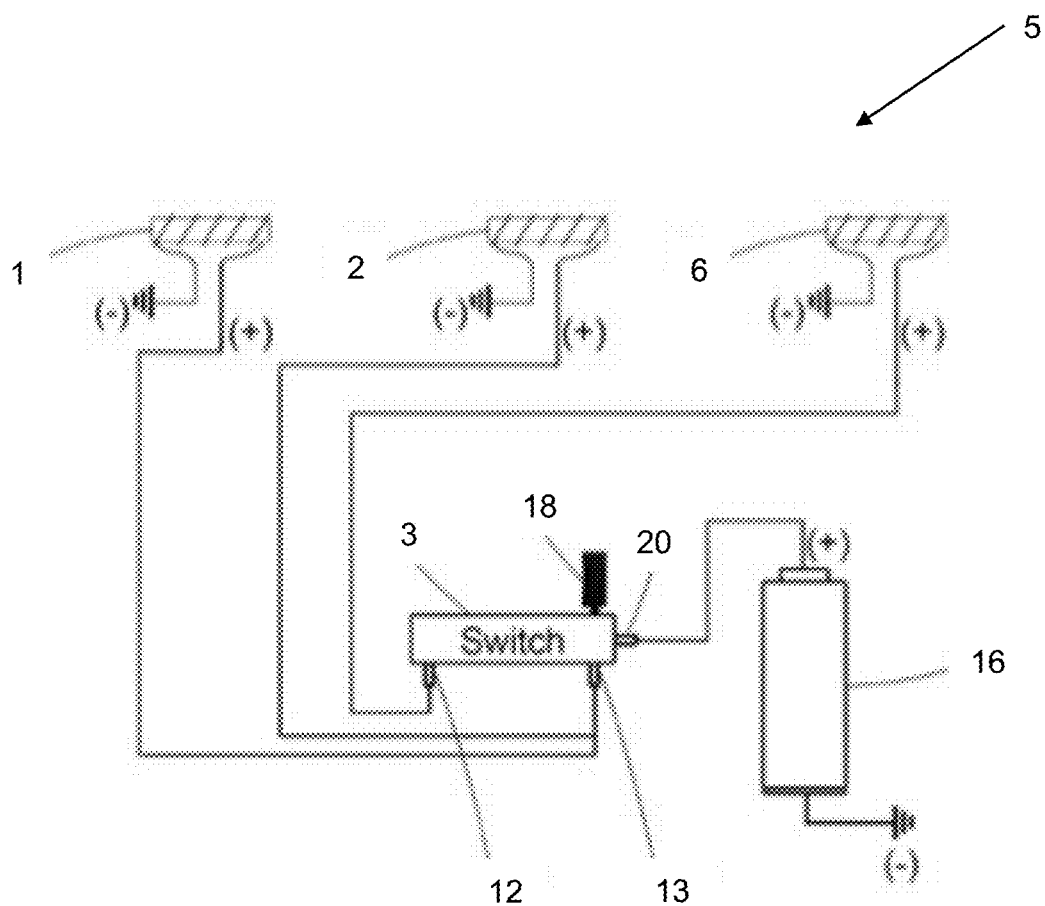
FIG. 8 shows a block diagram of the present invention with three heating elements, a switching element with one switch connected to two heating elements and a battery power source.

FIG. 8 displays another alternate configuration of the multi-element vaporizer system 5 with three heating elements, powered by a battery and including a two way switch for switching element 3. Switching element 3 is of the analog variety described above, in this case including a two position switch, and has 2 positive electrodes with first positive electrode 12 connected to the positive electrode of third heating element 6 and second positive electrode 13 connected to both the positive electrode of second heating element 2 and the positive electrode of third heating element 6. Switch 18 controls which of the heating elements are activated by switching element 3. When switch 18 is in the first position (left position), third heating element 6 receives electrical power and is activated. When switch 18 is in the second position (right position), first heating element 1 and second heating element 2 receive electrical power and are activated. Each heating element is also connected to ground as show in the figure. Battery 16 is connected to power electrode 20 could be a battery of any voltage or type as known in the art such as alkaline, nickel cadmium, nickel metal hydride or lithium ion.

Figure 9:
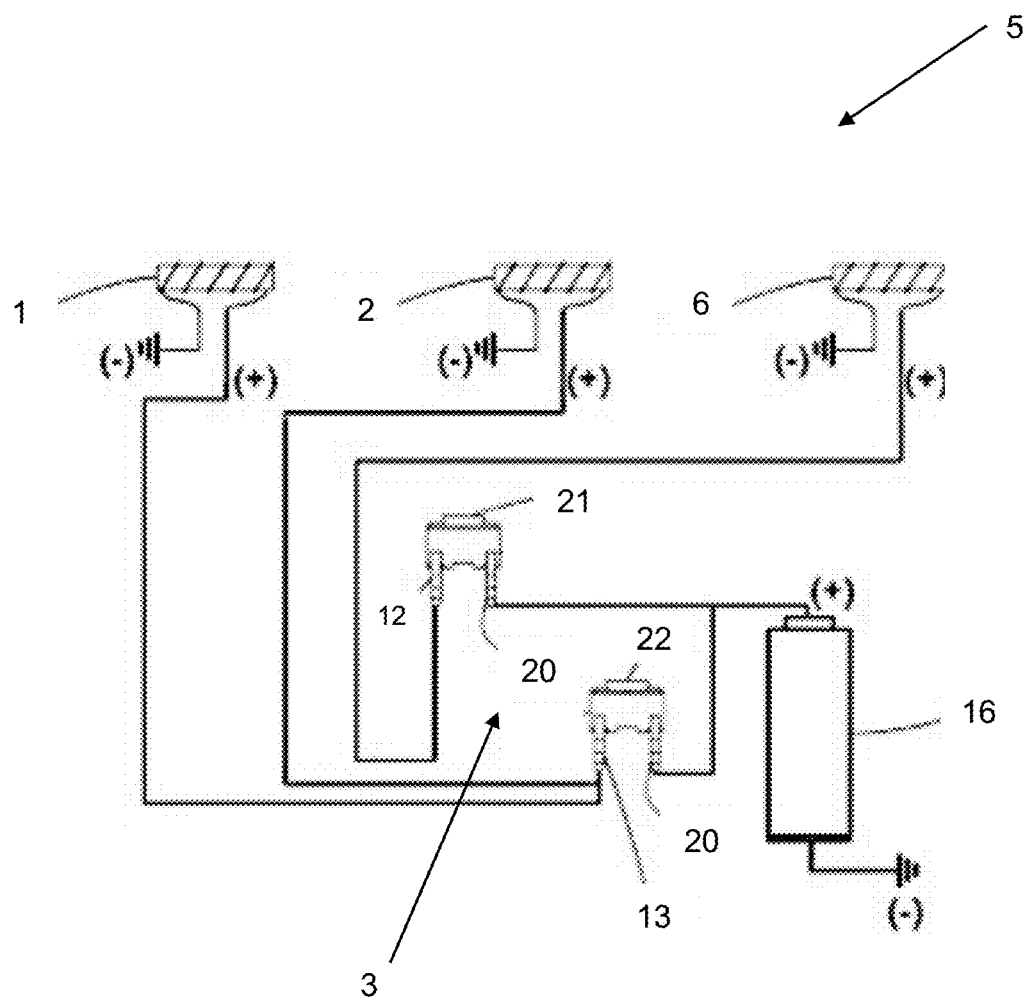
FIG. 9 shows a block diagram of the present invention with three heating elements, button switching elements and a battery power source.

FIG. 9 displays another alternate configuration of the multi-element vaporizer system 5 with three heating elements, powered by a battery and including two individual buttons that comprise switching element 3. Switching element 3 is of the analog variety described above, in this case including two individual buttons, first button 21 and second button 22. First button 21 includes first positive electrode 12 connected to the positive electrode of third heating element 6. When the user depresses first button 21, the electrical circuit between power electrode 20 (connected to the positive terminal of battery 16) and the positive electrode of third heating element 6 is completed, thus causing the heating element to heat. Similarly, second button 22 includes second positive electrode 13 connected to the positive electrodes of both first heating element 1 and second heating element 2. When the user depresses first button 22, the electrical circuits between power electrode 20 (connected to the positive terminal of battery 16) and the positive electrodes of first heating element 1 and second heating element 2 are completed, thus causing first heating element 1 and second heating element 2 to heat. First button 21 and second button 22 can be activated individually or together to customize which heating elements are activated. Each heating element is also connected to ground as show in the figure. Battery 16 is connected to power electrode 20 could be a battery of any voltage or type as known in the art such as alkaline, nickel cadmium, nickel metal hydride or lithium ion.

Figure 10:
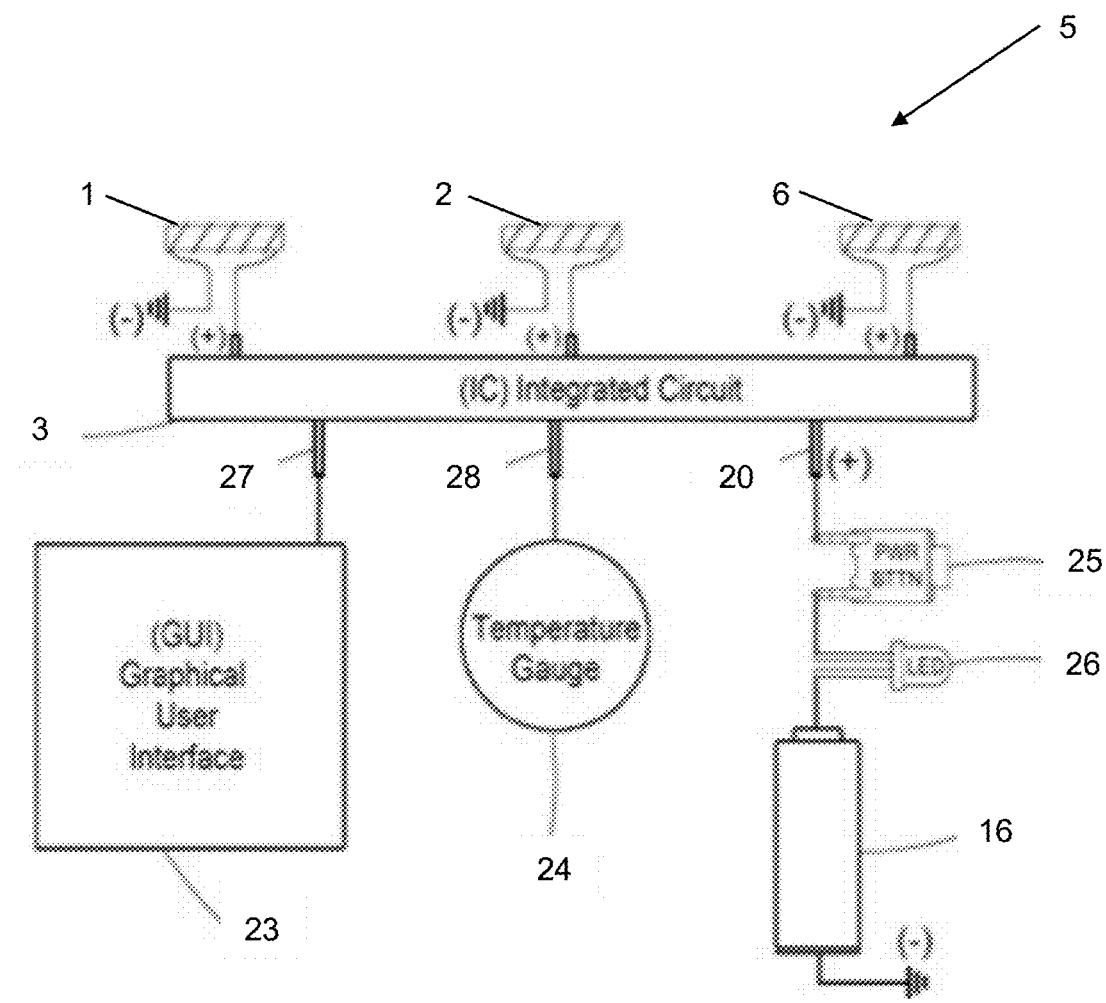
FIG. 10 shows a block diagram of the present invention with three heating elements, a digital switching element, a graphical user interface, a temperature gauge and a battery power source.

FIG. 10 shows a configuration of the multi-element vaporizer system 5 that includes three heating elements and a digital switching element 3. In this configuration, the switching element 3 is of the digital variety with three power outputs connected to first heating element 1, second heating element 2 and third heating element 6. Switching element 3 is comprised of an integrated circuit/micro-controller that controlled by a graphical user interface (GUI) 23 that is stored in system software. Details of GUI 23 will be discussed in subsequent figures. GUI 23 allows the user, through a screen, to control the activation, duration and intensity of the heat output by each of the three heating elements in this configuration. The digital switching element 3 in this configuration has three inputs: (1) GUI input 27, (2) temperature gauge input 28 and (3) power electrode 20. Further, digital switching element 3 has three outputs in this configuration, each power to one of the three heating elements. Using controls available in GUI 23, the user can select the activation, duration and intensity of each heating element. The user can control variations of heating elements being activated at one time. The combinations are significant and increase with the number of heating elements in the device which is not limited. Temperature gauge 24 allows the user to monitor the temperature of each heating element to detect when high temperatures are reached that could result in over vaporization or burning of the material to be vaporized, or in the alternative, alert the user to low and inefficient temperatures that also result in poor vaporization. These temperatures are displayed in GUI 23 and are monitored by the system software. The user may select manual temperature adjustment for greater control or automated adjustment to allow the system software to adjust heating as needed for optimal vaporization. In this configuration, battery 16 is connected to an LED 26 to provide indication of power on or off as well as a power button 25 to turn the vaporizer on or off.

Figure 11:
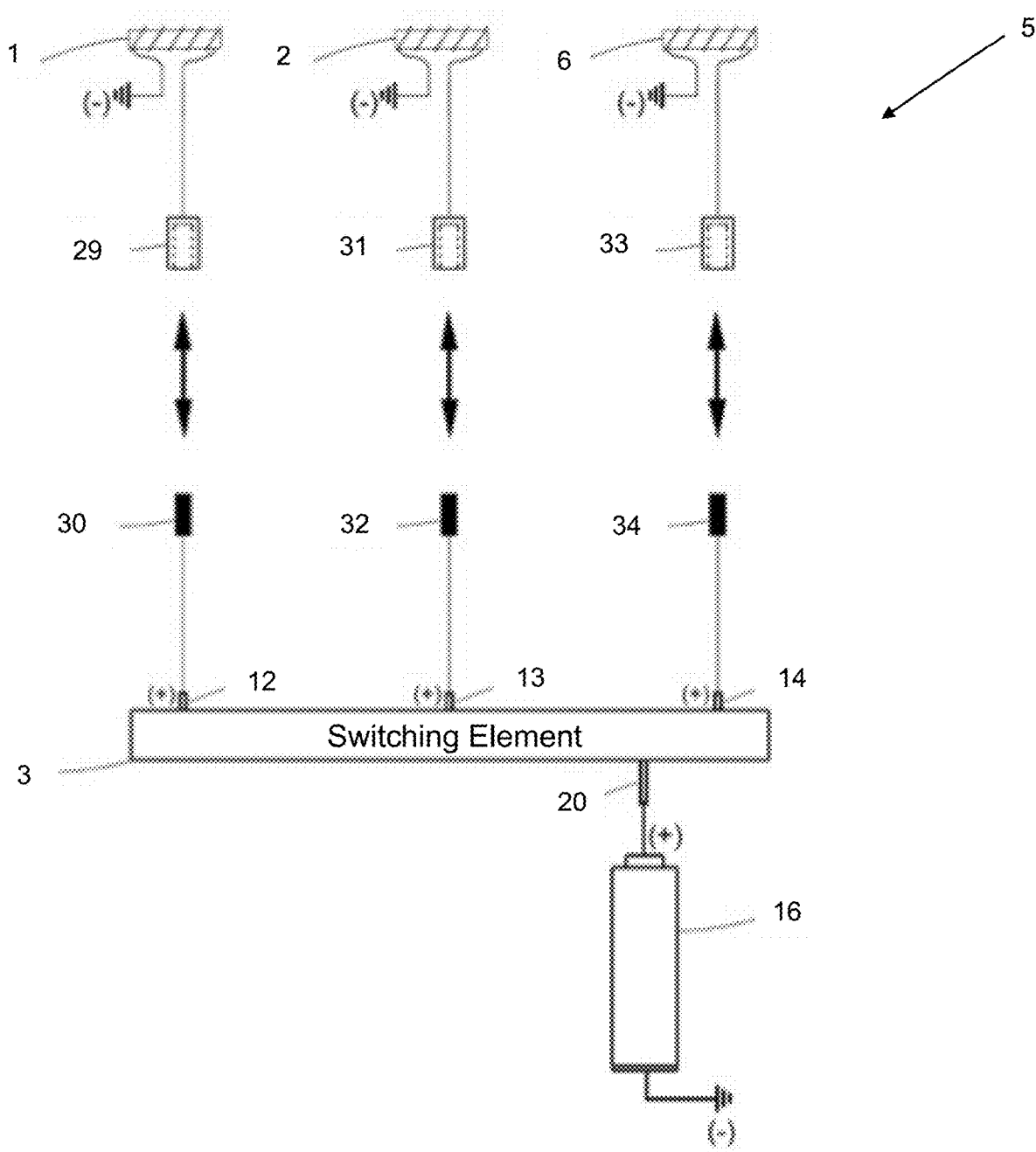
FIG. 11 shows a block diagram of the present invention with three plug-in heating elements, a switching element and a battery power source.

FIG. 11 displays a configuration of multi-element vaporizer system 5 where the heating elements are detachable from the switching element and power source by electrical connectors. In this example, switching element 3 has three positive power electrodes that control the activation, duration and intensity of each heating element. First positive electrode 12 is connected to male electrical connector 30 which is disposed to fit in female electrical connector 29 which is connected directly to first heating element 1. Male electrical connector 30 and female electrical connector 29 are designed to be easily connected and disconnected from each other. Similarly, second positive electrode 13 is connected to second male electrical connector 32 and slots into second female connector 31, which is connected to second heating element 2. Finally, third positive electrode 14 is connected to third male electrical connector 34 and slots into third female connector 33, which is connected to third heating element 6. This configuration may be repeated for any number of heating elements. Battery 16 is connected to switching element 3 by positive electrode 20. In this configuration of the preferred embodiment of the present invention, press fit or magnetic electrical connectors for male and female electrical connectors are used but may other types of electrical connections are imagined and could be used within the scope of the claims.

Figure 12:
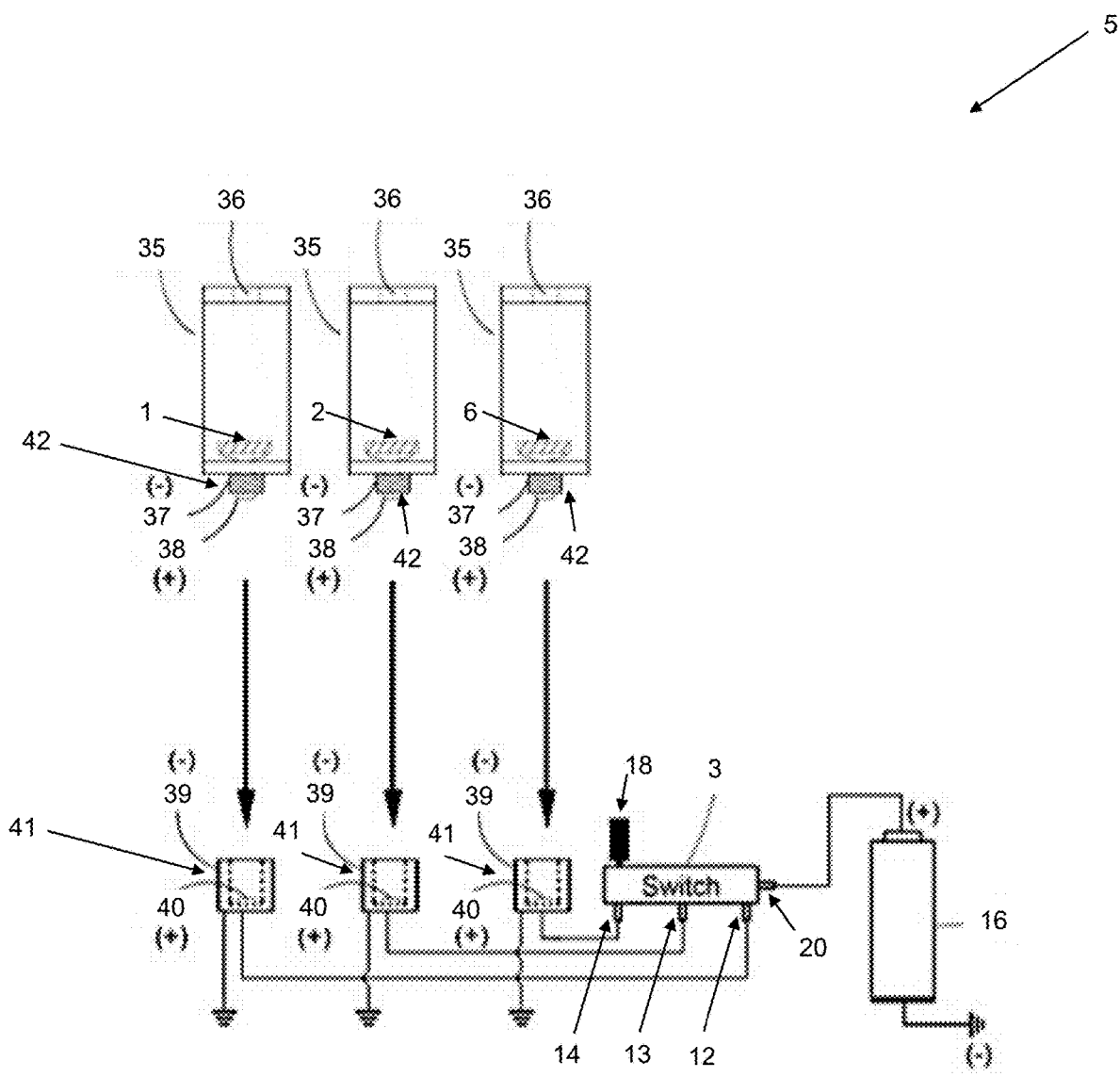
FIG. 12 shows a block diagram of the present invention with three screw-in heating elements, a toggle switching element and a battery power source.

FIG. 12 shows a configuration of multi-element vaporizer system 5 with three detachable cartridges each with individual heating elements addressable through switching element 3 and screw type connectors. Each cartridge 35 encloses a cavity that contains a material to be vaporized and heating element 1. Air passage 36 is disposed at the opposite end of the cartridge from the heating element and allows the user to inhale air through the device and thus the vaporized material. A complementary air passage (not shown) is disposed at the opposite end of the cartridge from air passage 36 to allow the user to draw air through the cavity and over the heating element and vaporizer material. Cartridge 35 includes a male threaded screw connector 42 including an outer thread 37 connected to ground and a center post 38 that connects to the power electrode/source. Female threaded screw connector 41 includes an outer thread 37 that couples with inner thread 39 when the cartridge is screwed in, also connected to ground. When the cartridge is screwed into the female threaded screw connector 41, center post 38 connects to inner electrode 40, which is connected to power. The cartridge components and connectors are the same for each cartridge, but the heating elements are numbered separately to indicate their individual control by switching element 3: first heating element 1 is connected to first positive electrode 12, second heating element 2 is connected to second positive electrode 13 and third heating element 6 is connected to third positive electrode 14. Power electrode 20 is connected to battery 16 and switch 18 controls which of the heating elements is activated.

Figure 13:
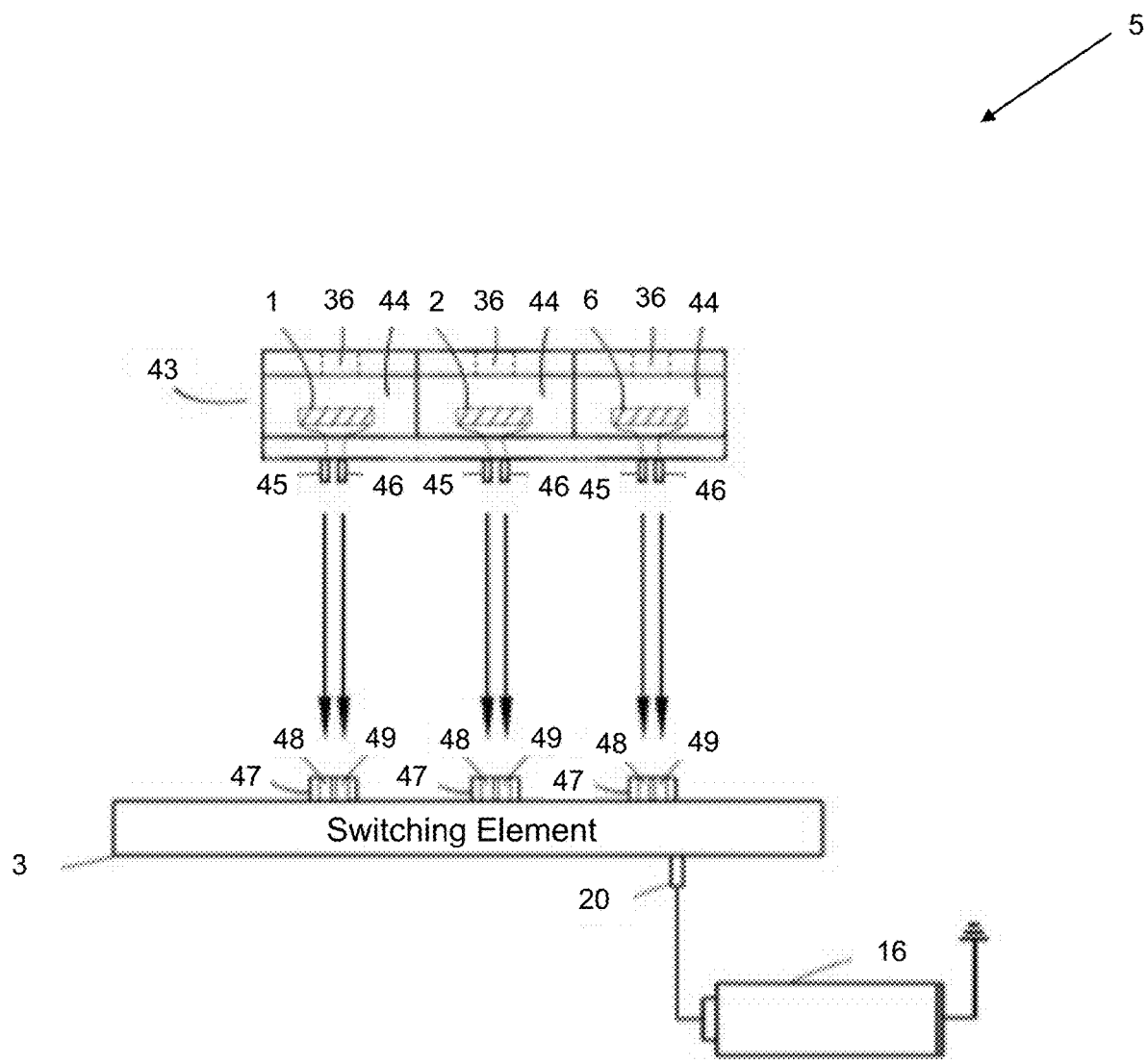
FIG. 13 shows a block diagram of the present invention with three plug-in heating elements in a shared housing cavity, a switching element and a battery power source.

FIG. 13 shows a configuration of the multi-element vaporizer system 5 with a multi-chamber plug-in cartridge 43. The multi-chamber plug-in cartridge 43 has three heating elements, first heating element 1, second heating element 2 and third heating element 6. Each heating element is contained within a cavity 44 and each cavity has an air passage 36. A complementary air passage (not shown) is disposed at the opposite end of the cartridge from air passage 36 to allow the user to draw air through the cavity and over the heating element and vaporizer material. The multi-chamber plug-in cartridge 43 has three sets of electrical posts on its underside, each labeled first post 45 and second post 46. Switching element 3 includes three press-fit receptacles 47, each comprising a first receptacle 48 and a second receptacle 49. First post 45 corresponds to first receptacle 48 and second post 46 corresponds to second receptacle 49 and when pressed together, they form an electrical connection. This configuration allows the user to vaporize three different substances in the three cavities and vaporize them in many combinations of activation, duration and intensity as previously described.

Figure 14:
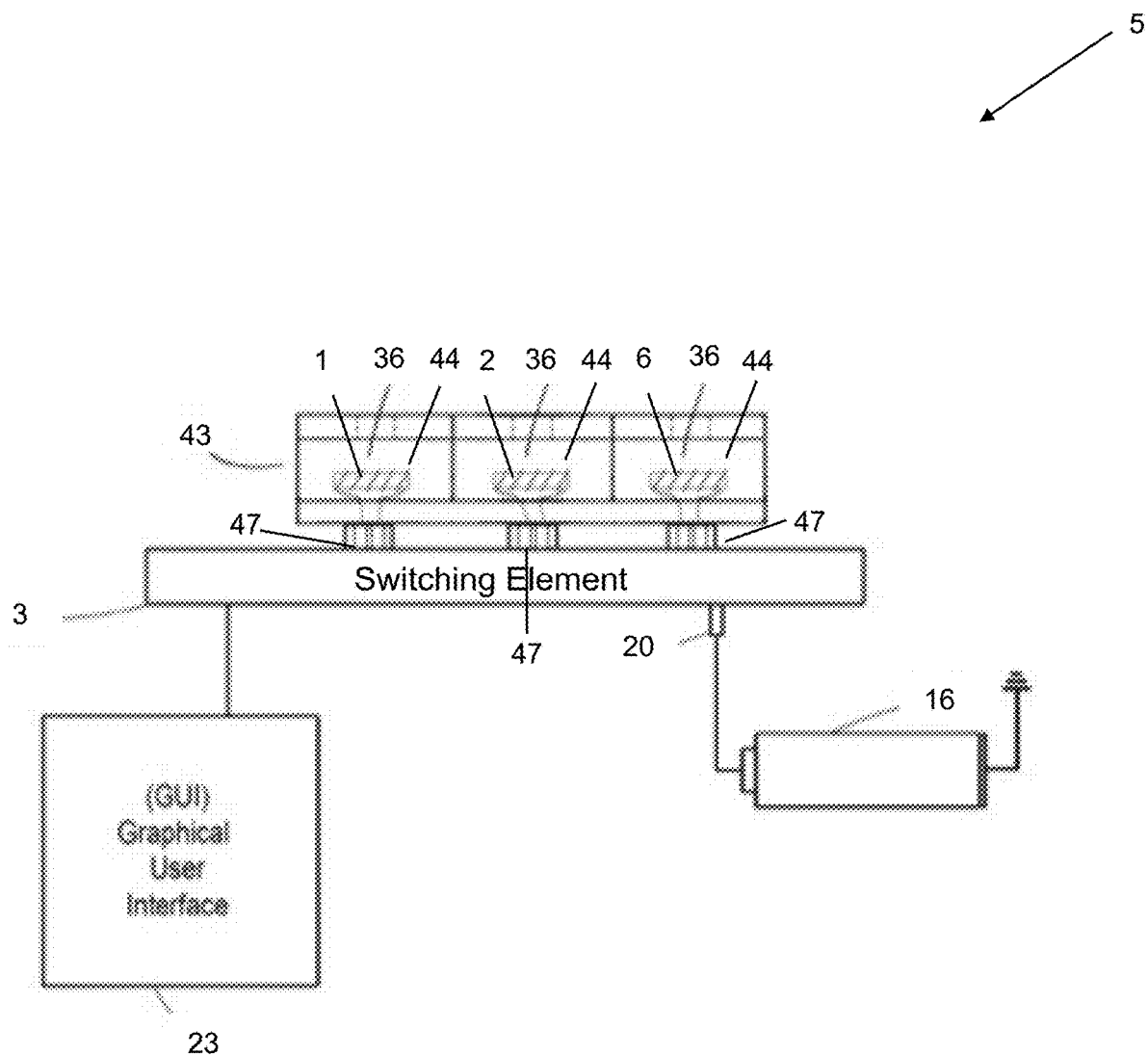
FIG. 14 shows a block diagram of the present invention with three plug-in heating elements in a shared housing cavity, a digital switching element, a GUI control system and a battery power source.

FIG. 14 shows the multi-element vaporizer system 5 with the multi-chamber plug-in cartridge 43 seated in the press-fit receptacles 47 and thus connected to the switching element 3 and battery 16. This configuration also includes GUI 23 for control of switching element 3. As with other configurations, battery 16 is connected to power electrode 20 could be a battery of any voltage or type as known in the art such as alkaline, nickel cadmium, nickel metal hydride or lithium ion.

Figure 15:
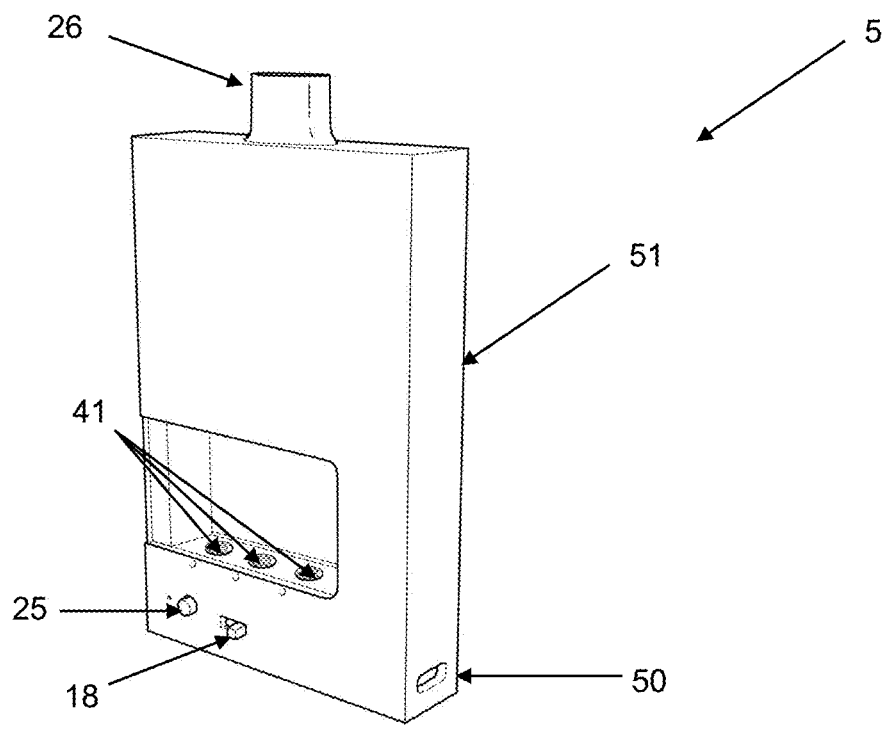
FIG. 15 shows a configuration of the housing of the present invention with power buttons and toggle switches.

FIG. 15 shows an example of the complete multi-element vaporizer system 5 with its housing 51. Air passage 26 is disposed at the top of housing 51 allowing the user to draw air through the cavities where the various materials are vaporized by individual heating elements. This configuration has spaces for three cartridges with screw type connectors 41. Each cartridge can contain a different material and each heating element can be activated by switch 18. Power button 25 turns the unit on and off. Complementary air passage 50 allows outside air to be drawn through the cavities as the user draws air through air passage 26. The device as configured allows a user to vaporize three different materials, in three different cartridges while individually controlling the heating element for each material. In this configuration, each cartridge may also have a dedicated LED (light emitting diode) that lights when that cartridge is powered via the switching element. These LEDs can be in various colors and provide indication of ready to be powered, powered (via the switching element) and a visual indicator for when the cartridge needs to be refilled with smokable material. Other visual indications are possible, such as flashing of the LEDs depending on the message to be sent to the user. For example, the LED could flash green while the heating element is powering up and the glow solid green when it is ready to be utilized. The LED could flash yellow when the contents of the cartridge are starting to get low and flash red when it is empty. Other examples include glowing orange while heating and turning to red when the material has been heated as much as recommended.

Figure 16:
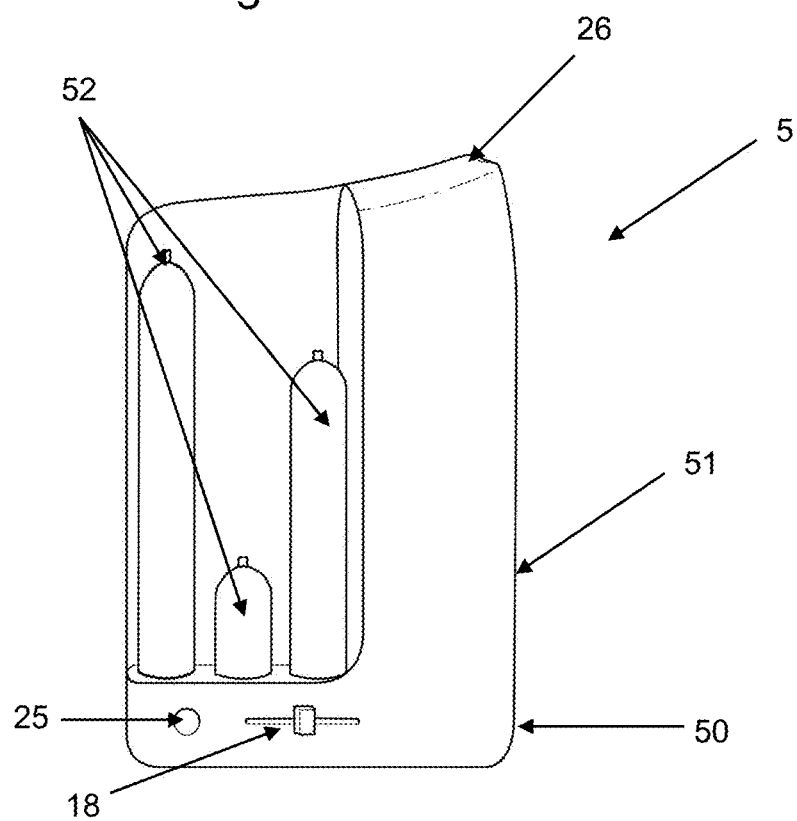
FIG. 16 shows a configuration of the housing of the present invention with power buttons and toggle switches.

FIG. 16 shows a different exterior view and configuration of the complete multi-element vaporizer system 5 with its housing 51. Air passage 26 is disposed at the top of housing 51 allowing the user to draw air through the cavities where the various materials are vaporized by individual heating elements. This configuration has spaces for three cartridges with either screw type connectors 41 or press-fit receptacles 41. Each cartridge can contain a different material and each heating element can be activated by switch 18. Power button 25 turns the unit on and off. Complementary air passage 50 allows outside air to be drawn through the cavities as the user draws air through air passage 26. The device as configured allows a user to vaporize three different materials, in three different cartridges while individually controlling the heating element for each material. Individual LEDs for each cartridge/heating element, with visual indications as described above, can also be included in this configuration.

Figure 17:
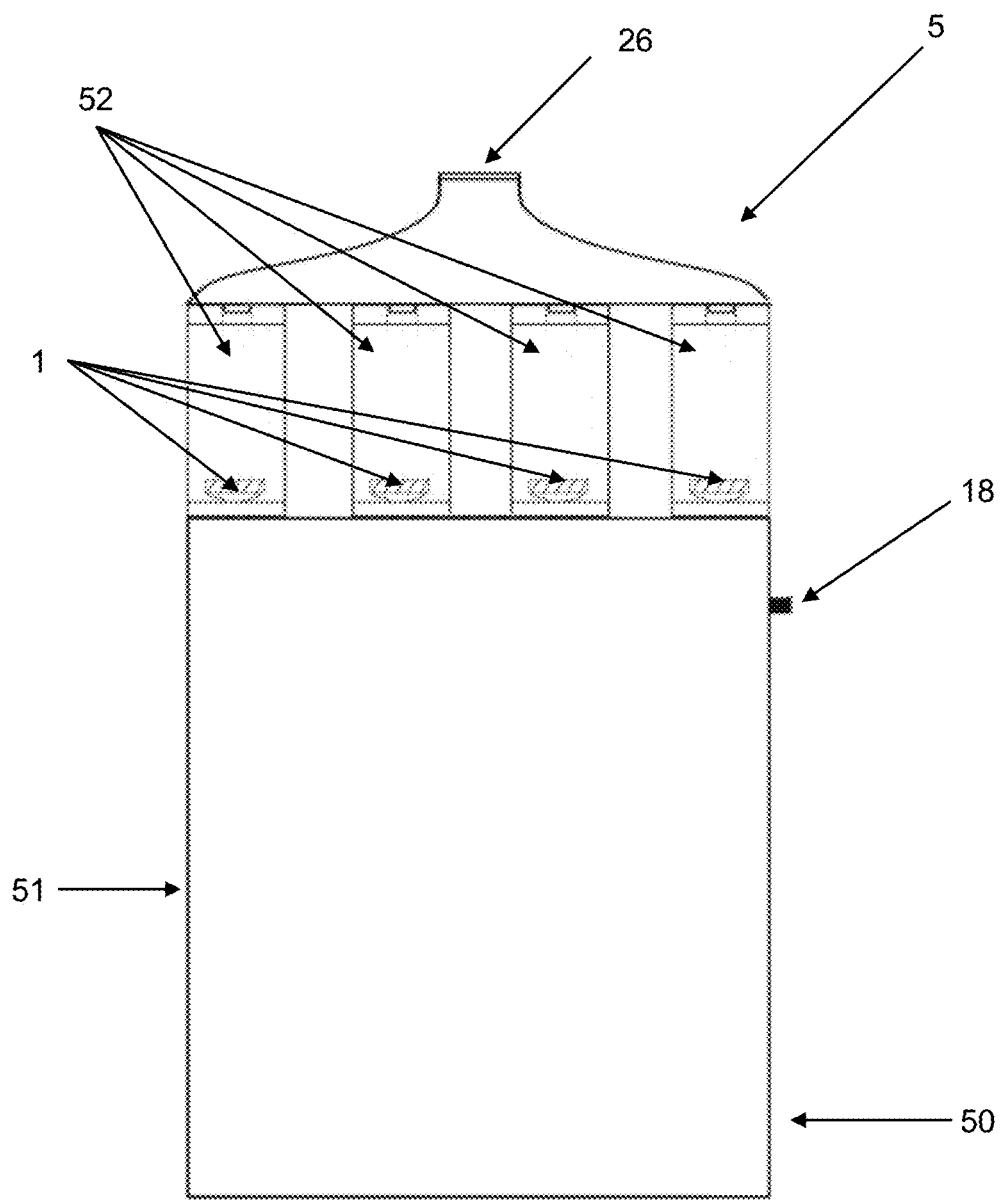
FIG. 17 shows a configuration of the housing of the present invention with four cavities and heating elements.

FIG. 17 shows another view of a different configuration of the complete multi-element vaporizer system 5 with four vaporizer cartridges in housing 51. The user of the device inhales through air passage 26 at the top while air is drawn through complementary air passage 50 at the bottom. Switch 18 controls switching element 3 which in turn controls which heating element 1 is activated and for what duration and intensity. Each vaporizer cartridge 52 contains a heating element and is of the pod variety well known in the art. In this configuration, the user can mix vaporizer output from 4 different and varied substances. Individual LEDs for each cartridge/heating element, with visual indications as described above, can also be included in this configuration. In this configuration, vaporizer cartridges can be of the press-fit variety as described above or with magnetic connectors that hold the cartridge in place.

Figure 18:
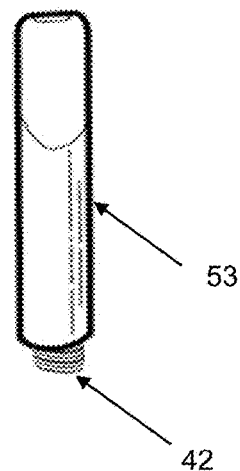
FIG. 18 shows a cavity of the screw-in attachment type.

FIG. 18 shows a standard threaded vaporizer cartridge 53 well known in the art. This threaded vaporizer cartridge 53 includes a male threaded screw connector 42 that fits in a female threaded screw connector known in the art. An example of a common threaded vaporizer cartridge is the "510" thread cartridge but any threaded vaporizer cartridge would comport with the elements of the claim. Individual LEDs for each cartridge/heating element, with visual indications as described above, can also be included in this configuration.

Figure 19:
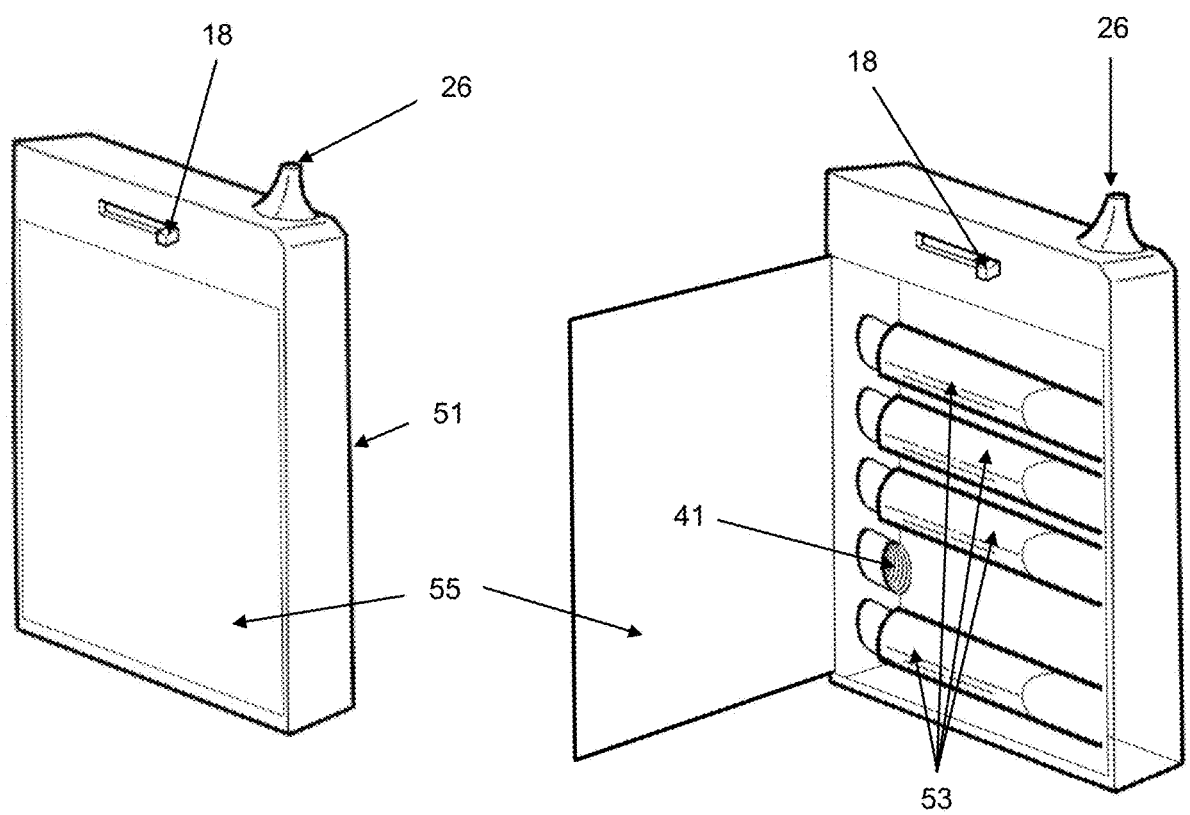
FIG. 19 shows a configuration of the housing of the present invention with five screw-in cavities and heating elements, and a door.

FIG. 19 shows a multi-element vaporizer with a housing 51 including door 55. Door 55 can be seen in open and closed positions. User draws air through air passage 26 to inhale vaporized material. Switch 18 controls switching element 18 to determine which of the heating elements in the device will be heated. In this configuration, the housing holds five standard threaded vaporizer cartridges 53 that connected to the housing with female threaded screw connectors 41. Individual LEDs for each cartridge/heating element, with visual indications as described above, can also be included in this configuration.

Figure 20:
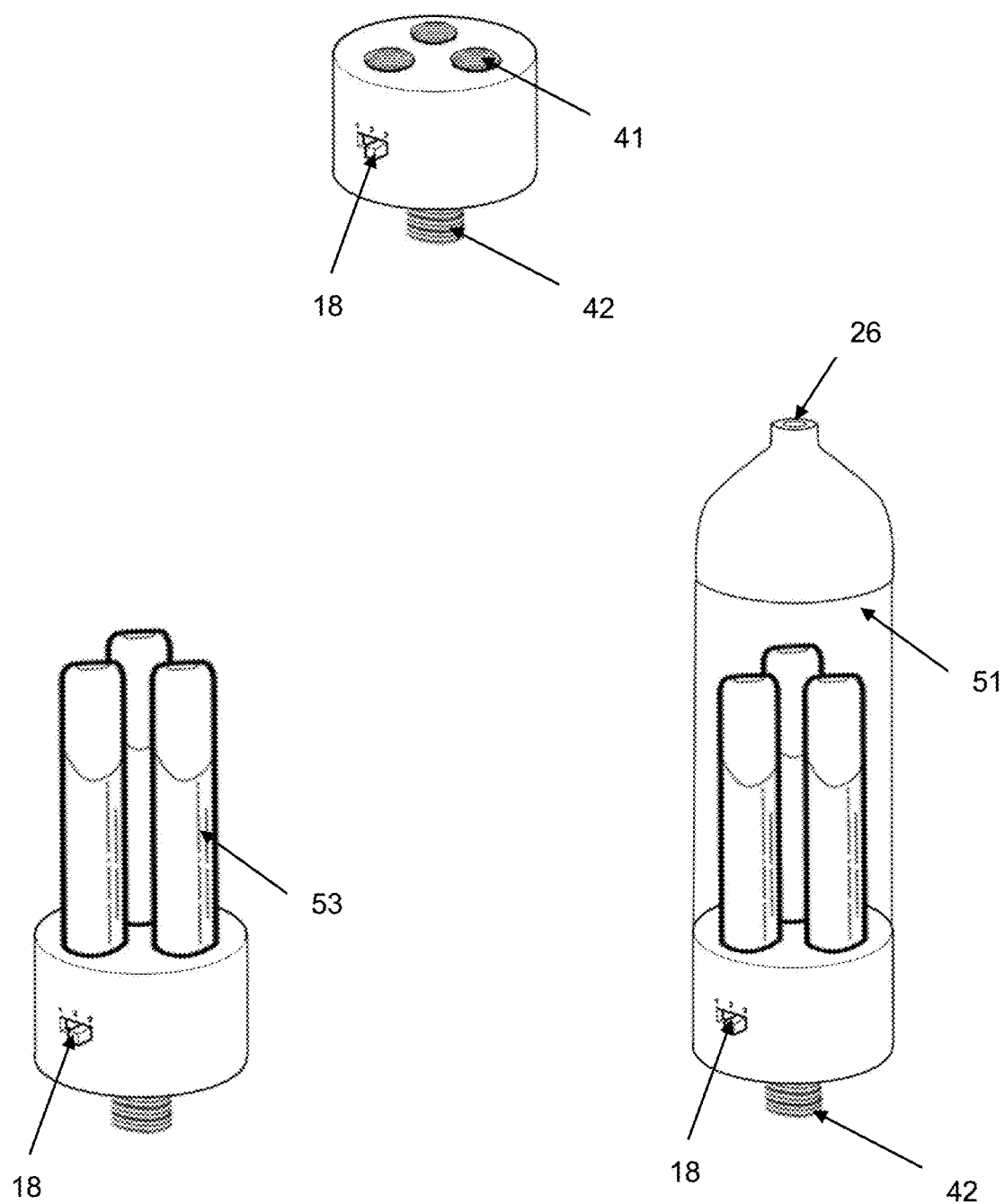
FIG. 20 shows a configuration of the housing of the present invention with three screw-in cavities and heating elements, and a dome.

FIG. 20 displays an alternate configuration of the multi-element vaporizer system 5 with three standard threaded cartridges 53 in housing 51. The base of the unit includes a threaded male screw connector 42 that couples with a standard vaporizer battery well known in the art (not shown). The top of the base includes three female threaded screw connectors 41 that support standard threaded cartridges 53. Each standard threaded cartridge 53 includes a heating element (not shown). The activation of each heating element is controlled by switch 18 which activates switching element 3 (not shown) as previously described. Housing 51 includes air passage 26 for inhaling vaporized material. Individual LEDs for each cartridge/heating element, with visual indications as described above, can also be included in this configuration.

Figure 21:
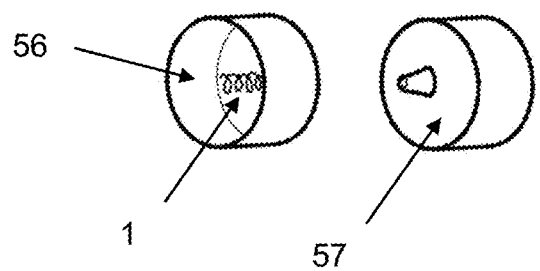
FIG. 21 shows a configuration of the housing of the present invention with 12 permanent cavities with removable lids and a door.
Figure 21:
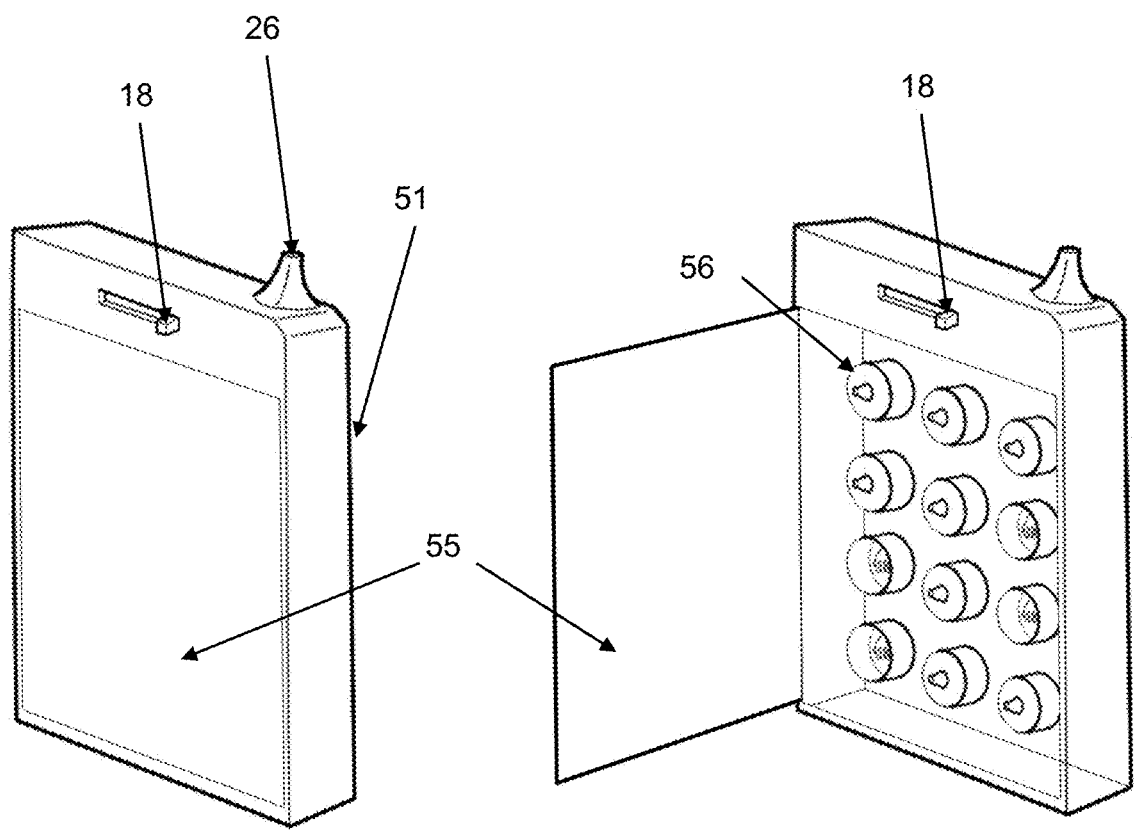

FIG. 21 displays another alternate configuration for the multi-element vaporizer system with removable lid cartridges 56. These removable lid cartridges 56 include removable lid 57 so that the user can manually insert any chosen material for vaporization. Heating element 1 provides the heat source for vaporization and is controlled by switching element 3 (not pictured) The housing 51 in this example holds 12 plug-in cartridges for a large variety of included materials. Switch 18 allows the user to select any of the 12 cartridges for vaporization. Door 55 provides easy access to add and remove cartridges or material. Individual LEDs for each cartridge/heating element, with visual indications as described above, can also be included in this configuration. In addition to plug-in type cartridges, cartridges using magnetic connectors may also be used in this configuration.

Figure 22:
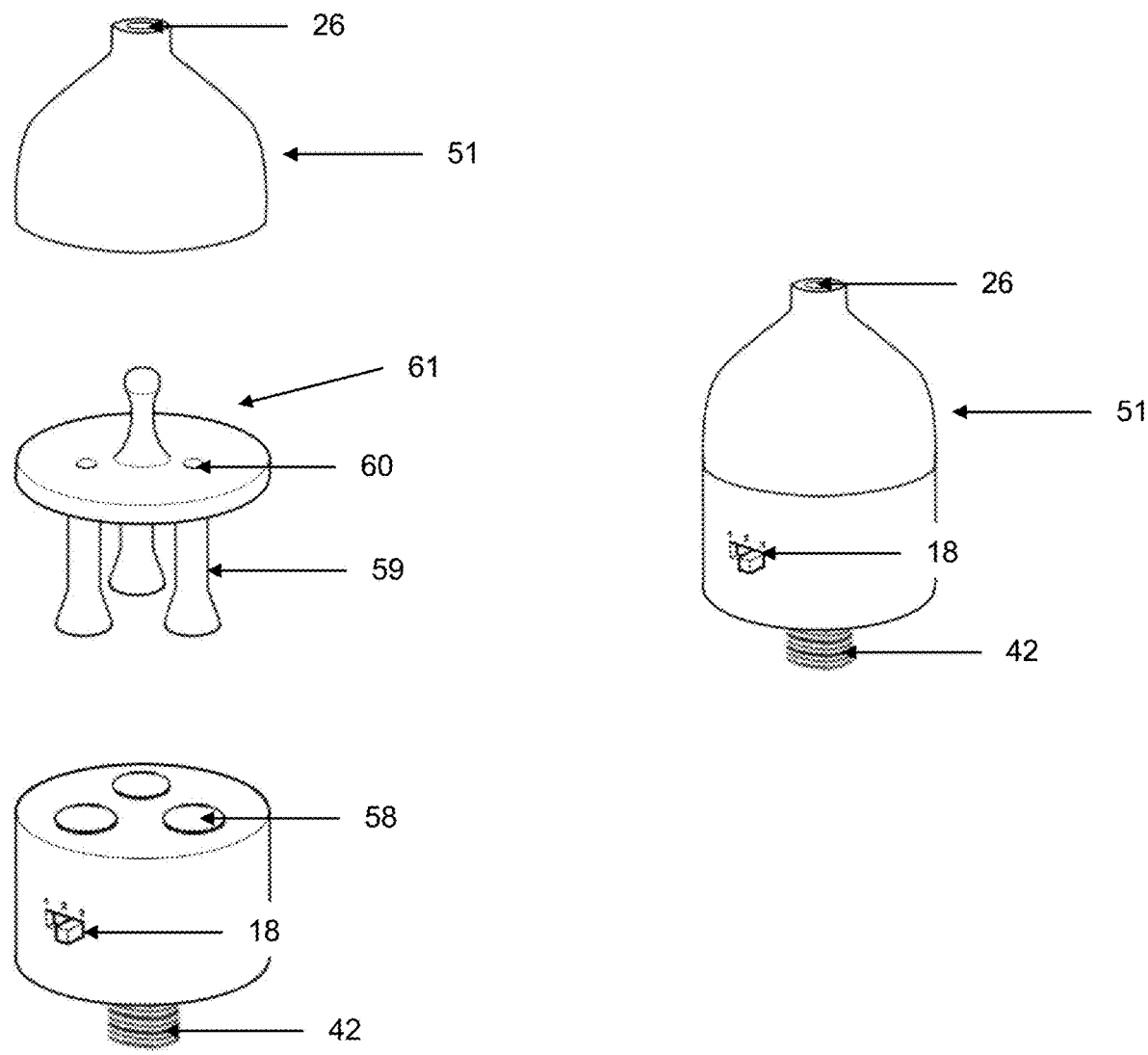
FIG. 22 shows a configuration of the housing of the present invention with three well type cavities with heating elements, a cap and a dome.

FIG. 22 shows a variation of the multi-element vaporizer system with three material wells 58 for inserting material for vaporization. Each well contains a heating element (not shown) that is connected to the switching element 3 for individual activation by switch 18. To utilize this device, the user places their chosen material to be vaporized in each well 58. The user then places cap 61 such that each leg 59 is secured within a well 58. The user then attaches the housing 51 to the cap 61. Once the device is assembled, the user inhales vaporized material through air passage 26 via cap passage 60. In this way, the material in each well can be vaporized individually to the user's specification by utilizing switch 18 to activate heating elements individually. Male threaded screw connector 42 allows this device to be connected to any standard vaporizer battery with a female threaded screw connector 41.

Figure 23:
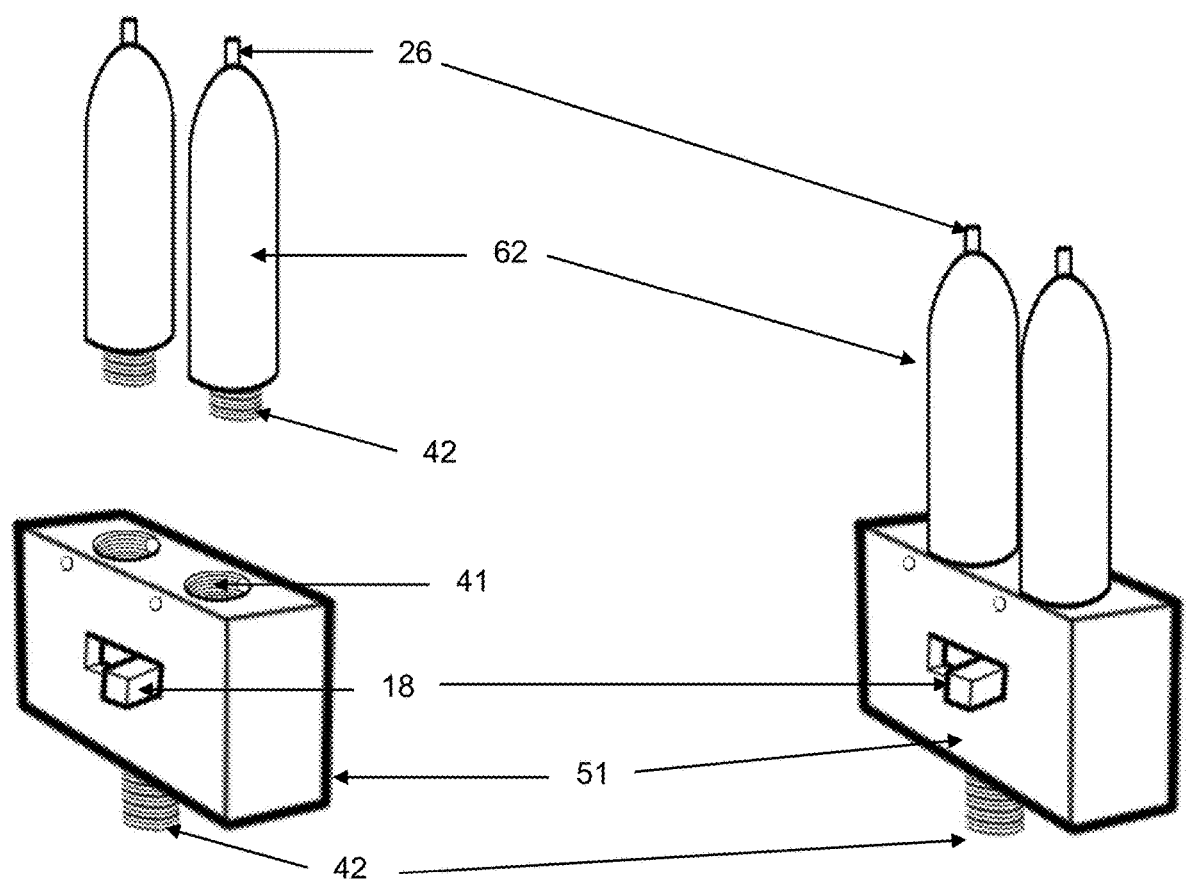
FIG. 23 shows a configuration of the housing of the present invention with two screw-in type cavities with heating elements.

FIG. 23 shows a configuration of the multi-element vaporizer cartridge 5 with two individual domed cartridges 62. Domed cartridge 62 has a male threaded screw connector 42 at one end, a cavity in the center containing a material for vaporization and a heating element, and an air passage 26 at the top. Each domed cartridge 62 threads into female threaded screw connector 41 formed in the top of housing 51. The user may utilize switch 18 to control switching element 3 to select which heating element will be activated. The user inhales the vaporized substance through air passage 26 at the top of domed cartridge 62. The bottom of housing 51 includes a male threaded screw connector 42 that connects to standard vaporizer batteries well known in the art. Individual LEDs for each cartridge/heating element, with visual indications as described above, can also be included in this configuration.

Figure 24:
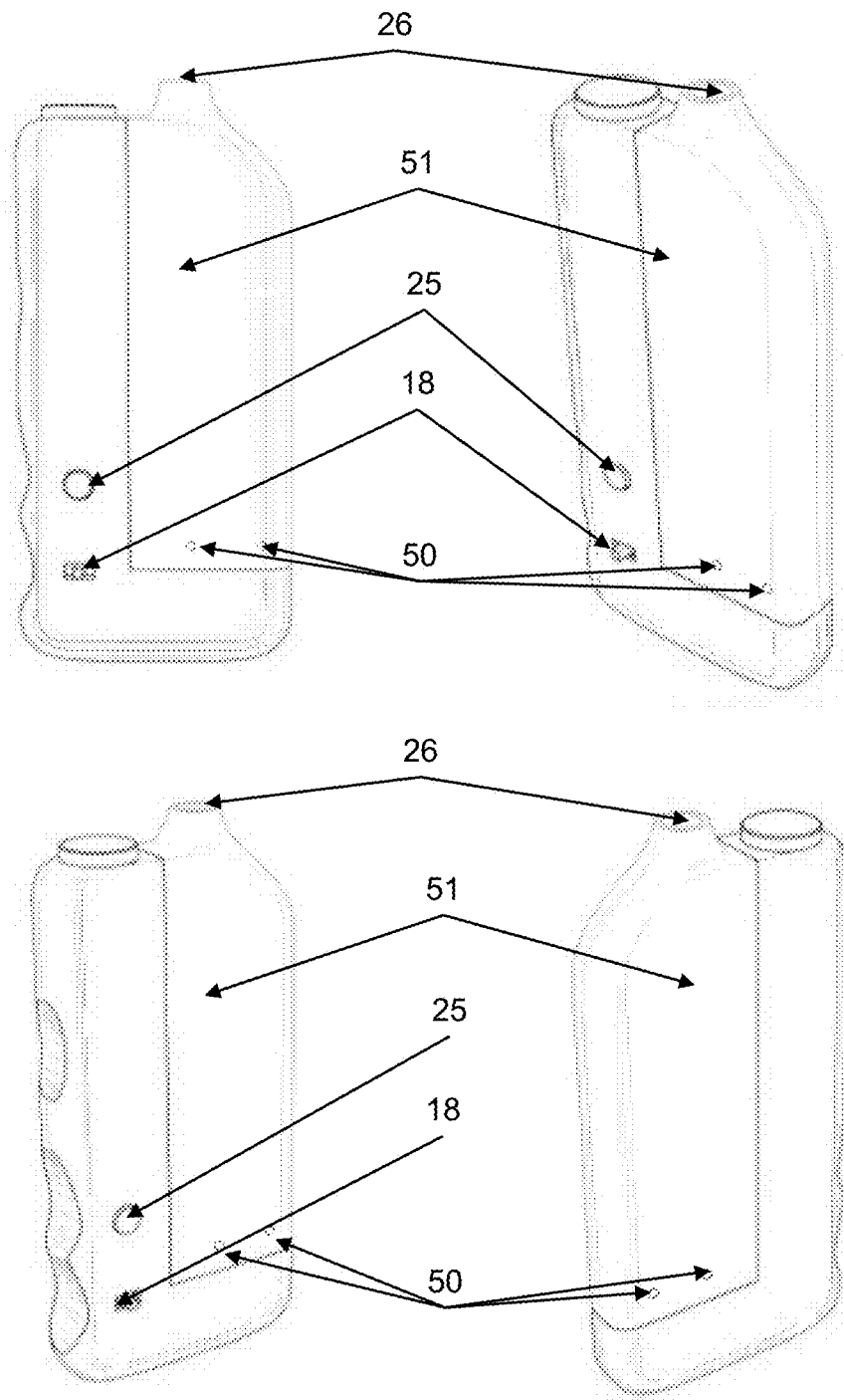
FIG. 24 shows a configuration of the housing of the present invention with a shared housing and air passages.

FIG. 24 shows the exterior of housing 51 another configuration of multi-element vaporizer system 5. Located at the top of housing 51, air passage 26 allows the user to inhale vaporized material vaporized by heating elements contained within housing 51. Power switch 25 turns the device on and off. Switch 18 controls switching element 3 and this which heating element is activated. Complimentary air passage 50 provides an air inlet as user draws air through air passage 26. As with other variations of the multi-element vaporizer system 5, this configuration allows the user to select which heating element is activated and thus the mixture of vaporized materials inhaled through air passage 26. Individual LEDs for each cartridge/heating element, with visual indications as described above, can also be included in this configuration. This configuration allows screw-in, plug-in, press-fit or magnetic type cartridges.

Figure 25:
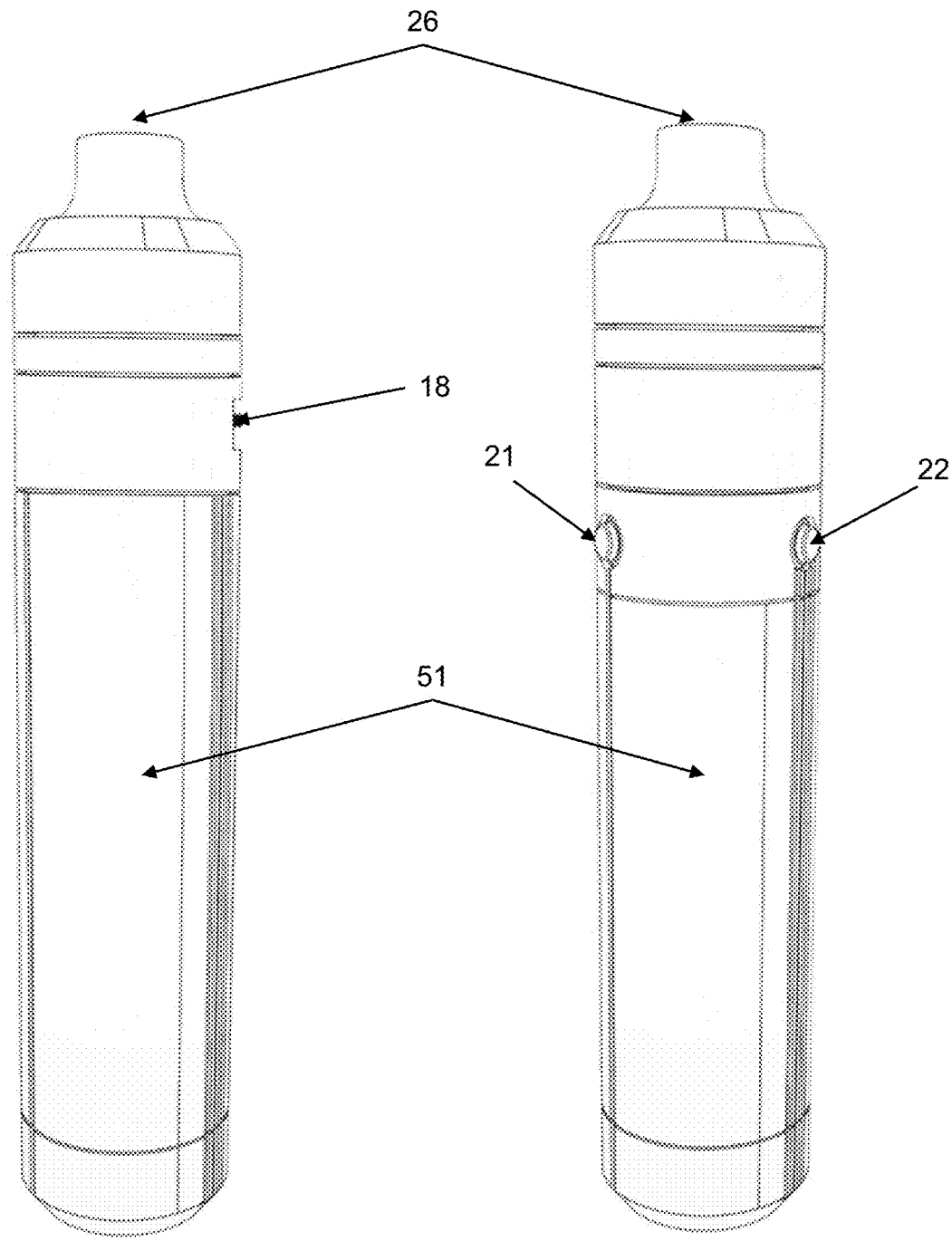
FIG. 25 shows an alternate configuration of the housing of the present invention with a shared housing and air passages.

FIG. 25 shows two essentially cylindrical housings 51 of the multi-element vaporizer system 5. Both units have air passage 26 at the top of housing 51. The heating elements (two) in the unit on the left side are controlled by switch 18 which is connected to switching element 3. The unit on the right is controlled by a first push button 21 and a second push button 22. Individual LEDs for each cartridge/heating element, with visual indications as described above, can also be included in this configuration.

Figure 26:
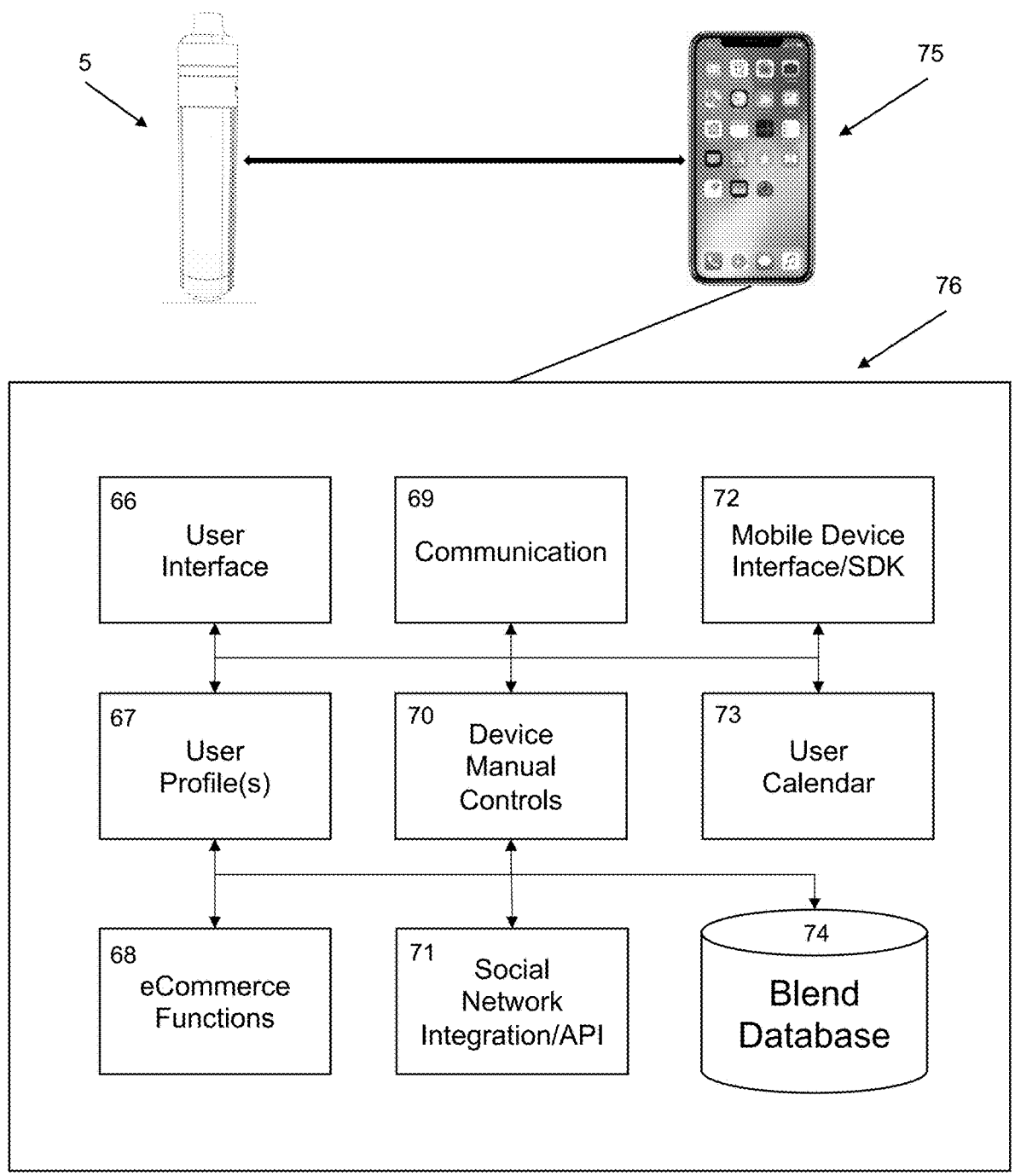
FIG. 26 shows a block diagram of the mobile application for the portable vaporizer.

FIG. 26 is a block diagram of a mobile application to control multi-element vaporizer 5. Mobile device 75 shown in the figure is an Apple iPhone running iOS but could be any device running the Google Android mobile operating system, any other suitable mobile operating system allowing third party applications or non-mobile computer systems. Mobile application 76 comprises a number of major functionalities displayed in the block diagram. This list is not meant to be comprehensive but rather to show the core and unique functions required by the present system. Mobile device interface/SDK 72 is the functionality that allows the third party developed application to interface with the mobile operating system to access operating system functionality and hardware functions. These tools are common to mobile operating systems and are unique to each variety of mobile operating system. Communication block 69 enables the mobile application to access the mobile phone communications hardware, specifically allowing access to Bluetooth for communicating with the multi-element vaporizer device 5 and mobile/cellular data via 3G/4G/LTE/5G mobile data networks and WIFI for communicating with the internet. User interface 66 provides the key application controls to allow the user to set up a user profile, access the controls for the vaporizer, user calendar, blend database and any other functions of the application. The user interface 66 allows the user to manually control the activation, active time, heating intensity/temperature and specific patterns of each of those vaporizer controls for each heating element. The user interface 66 also allows the user to select from pre-populated heating patterns for various combinations of substances from blend database 74. Additionally, the user interface 66 allows the user to save their specific preferences in blend database 74. User profile 67 allows the user to set up a user profile for use on the application and all connected internet sites. This usually comprises a user name, password, email address but further allows stored shipping/billing addresses and credit card information for ecommerce purchases. Manual device controls 70 allow the user to set the following configurations for each heating element in the attached multi-element vaporizer system: (a) activation—turning the element on, (b) timer—length of time the heating element is activated, (c) intensity/temperature—the temperature of the heating element, and (d) pattern—the user may set up a timed pattern of heating element activation and temperature. Any combination of these manual configurations may be saved as a user blend configuration and stored in blend database 74.

User calendar 73 allows the user to setup vaporizer configurations for specific times of the day and days of the week. For example, if a user prefers a specific vaporizer configuration on weekday mornings, that information is stored in the user calendar and that vaporizer configuration is automatically loaded at that time. If the user has a different vaporizer configuration preference on weekend evenings, that configuration preference is stored in user calendar 73 and loaded automatically at the appropriate time. Ecommerce functions 68 allow the user to make direct purchases from various integrated ecommerce sellers offering supplies for the multi-element vaporizer system such as batteries, cartridges (empty and loaded with materials), various *Cannabis* flowers, oils, concentrates, hash and "shatters." These ecommerce functions allow the user to easily re-order any supplies necessary for their device.

Social network integration/API 71 allows access to known public APIs for social networks such as Facebook, Instagram and Twitter. A system user can share information about their vaporizer configurations and/or blend preferences directly to social media, as well as other appropriate information. Further, using public social media networks or private communication channels between devices, the vaporizer can be configured to make social connections (i.e. friends or followers in social media parlance) allowing sharing with these social connections after authorization by the user. On public social media networks, these social connections could be existing friend or follower lists but with an additional device or system software level authorization to share vaporizer information with that social connection. Additionally, the software is configured to allow the user to make social connections privately through the mobile application, system servers (not shown but well known in the art) and the internet or other network. Once these vaporizer social connections are authorized, the vaporizer can send or receive notifications from social connections such as a notification that a user or social connection is utilizing their device, a notification of what blends have recently be consumed by the user or a social connection and a request to share a current blend being consumed by a social connection. These notifications may occur within the mobile application, by push notification on a mobile device or by illuminating an LED on the actual vaporizer device.

Blend database 74 includes both an online database of various blend patterns/recipes/vaporizer configurations and stored local user vaporizer configurations/blend preferences. The public portion of blend database 74 is accessible to all devices that are internet connected. The user can share their preferences to the public database for use by other users on the system or keep their preferences private. Blend database 74 also includes some blend/vaporizer configurations developed by the application owners. It is also envisioned that blend database 74 includes blend/vaporizer configurations developed by brands and celebrities. Blend database includes the following types of information about *Cannabis* products: (a) type—indica, *sativa* or hybrid, (b) category—flower, oil, concentrate, hash or shatter, (c) strain—name of the particular *Cannabis* strain and (d) characteristics—THC/CBD percentages, user/professional reviews. This type of information is combined with multi-element vaporizer configurations such as activation, timing and temperature to allow nearly infinite combinations of *Cannabis* varieties with individual vaporization configurations to provide specific user mood effects. Blend database 74 contains both professional and user created blend patterns for many user options.

Blend database 74 includes further functionality that tracks the user's usage of the device and prompts the user to provide a rating for any new blend consumed. The goal is for the blend database 74 to include complete rating data for an blends consumed by the user or other users on the system. Rating could be a simple five star system or include specific ratings for other specific expected effect categories of the various materials to be vaporized, like mood or other defined characteristics such as a) calm, b) energy, c) sleep and d) anxiety reduction.

Blend database 74 may also interact with an optional Global Positioning System (GPS) sensor (optionally included in communication block 69). With the optional GPS sensor, blend database 74 may provide a user a "geofence experience" where the device tracks the user's specific blends in specific places, i.e. at home, at specific public locations, at a friend's home, or at an event venue. This geofence experience may provide the user with suggested blends consistent with their usage patterns at specific locations when the user enters a new or existing prior visited location.

Blend database 74 may also provide suggestions based on a user's specific mood. For example, the user could input that they are feeling "low energy" and the blend database could suggest blends that would provide an energy boost. The blend database 74 could include pre-defined moods or a natural language processor that asks the user to input words to describe their mood and while the database decodes an appropriate response and blend for that mood.

Blend database 74 may further include elements of artificial intelligence (AI) or machine learning to learn a user's preferences and make recommendations for existing or new blends. The blend database 74 tracks the user's usage over time, including substances included in cartridges, blends configured (i.e. mixes of various cartridges), GPS location data when particular blends are utilized, time of day/day of week data for blend usage and ratings by the user. With this information, blend database 74 builds a profile of the specific individual user. The system can compare the specific individual user profile with all user profiles in the system (anonymized by removing personally identifiable information) to determine blend recommendations for the user. The system can identify similar usage patterns across users and thus identify favorites across that type of user. Further, the system owner may program various suggested blends based on user profiles that can be recommended, or the system may build its own recommendations based on user profile data. These recommendations may be provided via the application/blend database for consumption options or via the ecommerce functions for product purchases.

Figure 27:
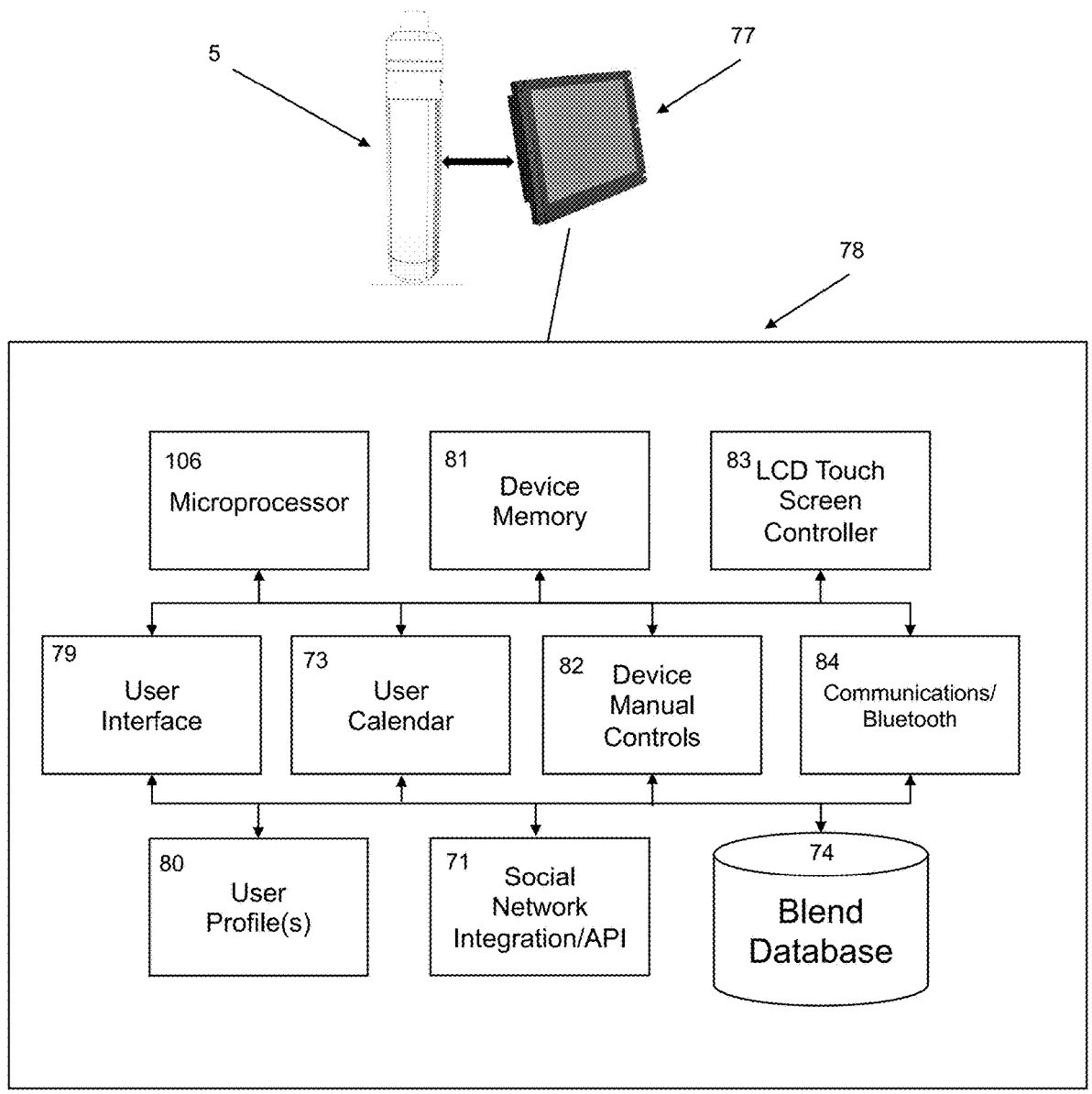
FIG. 27 shows a block diagram of the native application for the portable vaporizer.

FIG. 27 is a block diagram of native application 78 to control multi-element vaporizer 5. Native application 78 comprises the major functionalities displayed in the block diagram. This list is not meant to be comprehensive but rather to show the core and unique functions required by the present system. Native application 78 is accessed through touch controlled LCD screen 77 which is controlled by LCD and touch screen controller 83. Communication block 84 enables the native application to communicate via Bluetooth and optionally via mobile/cellular data 3G/4G/LTE/5G mobile data networks or WIFI for communicating with the internet. Microprocessor 106 provides computational power to process the native application. Microprocessor 106 is of the mobile microprocessor type manufactured by ARM, Intel, AMD and others well known in the art. User interface 79 provides the key application controls to allow the user to set up a user profile, access the controls for the vaporizer, blend database and any other functions of the application. The user interface 79 allows the user to manually control the activation, active time, heating intensity/temperature and specific patterns of each of those vaporizer controls for each heating element. The user interface 79 also allows the user to select from pre-populated heating patterns for various combinations of substances from blend database 74. Additionally, the user interface 66 allows the user to save their specific preferences in blend database 74. User profile 80 allows the user to set up a user profile for use on the application and all connected internet sites. This usually comprises a user name, password, email address may include further stored information for the device. While a user profile is enabled, it is not required to utilize the device. Device memory 81 is a standard non-volatile memory such as Flash memory used to store the device software and random access memory (RAM) connected to the microprocessor to store code and calculations during device operation.

Manual device controls 82 allow the user to set the following configurations for each heating element in the attached multi-element vaporizer system: (a) activation—turning the element on, (b) timer—length of time the heating element is activated, (c) intensity/temperature—the temperature of the heating element, and (d) pattern—the user may set up a timed pattern of heating element activation and temperature. Any combination of these manual configurations may be saved as a user blend configuration and stored in blend database 74.

User calendar 73 allows the user to setup vaporizer configurations for specific times of the day and days of the week. For example, if a user prefers a specific vaporizer configuration on weekday mornings, that information is stored in the user calendar and that vaporizer configuration is automatically loaded at that time. If the user has a different vaporizer configuration preference on weekend evenings, that configuration preference is stored in user calendar 73 and loaded automatically at the appropriate time.

Social network integration/API 71 allows access to known public APIs for social networks such as Facebook, Instagram and Twitter. A system user can share information about their vaporizer configurations and/or blend preferences directly to social media, as well as other appropriate information. Further, using public social media networks or private communication channels between devices, the vaporizer can be configured to make social connections (i.e. friends or followers in social media parlance) allowing sharing with these social connections after authorization by the user. On public social media networks, these social connections could be existing friend or follower lists but with an additional device or system software level authorization to share vaporizer information with that social connection. Additionally, the software is configured to allow the user to make social connections privately through the mobile application, system servers (not shown but well known in the art) and the internet or other network. Once these vaporizer social connections are authorized, the vaporizer can send or receive notifications from social connections such as a notification that a user or social connection is utilizing their device, a notification of what blends have recently be consumed by the user or a social connection and a request to share a current blend being consumed by a social connection. These notifications may occur within the mobile application, by push notification on a mobile device or by illuminating an LED on the actual vaporizer device.

Blend database 74 includes both an online database of various blend patterns/recipes/vaporizer configurations and stored local user vaporizer configurations/blend preferences. The public portion of blend database 74 is accessible to all devices that are internet connected. The user can share their preferences to the public database for use by other users on the system or keep their preferences private. Blend database 74 also includes some blend/vaporizer configurations developed by the application owners. It is also envisioned that blend database 74 includes blend/vaporizer configurations developed by brands and celebrities. Blend database includes the following types of information about *Cannabis* products: (a) type—indica, *sativa* or hybrid, (b) category—flower, oil, concentrate, hash or shatter, (c) strain—name of the particular *Cannabis* strain and (d) characteristics—THC/CBD percentages, user/professional reviews. This type of information is combined with multi-element vaporizer configurations such as activation, timing and temperature to allow nearly infinite combinations of *Cannabis* varieties with individual vaporization configurations to provide specific user mood effects. Blend database 74 contains both professional and user created blend patterns for many user options.

Blend database 74 includes further functionality that tracks the user's usage of the device and prompts the user to provide a rating for any new blend consumed. The goal is for the blend database 74 to include complete rating data for an blends consumed by the user or other users on the system. Rating could be a simple five star system or include specific ratings for other specific expected effect categories of the various materials to be vaporized, like mood or other defined characteristics such as a) calm, b) energy, c) sleep and d) anxiety reduction.

Blend database 74 may also interact with an optional Global Positioning System (GPS) sensor (optionally included in communication block 84). With the optional GPS sensor, blend database 74 may provide a user a "geofence experience" where the device tracks the user's specific blends in specific places, i.e. at home, at specific public locations, at a friend's home, or at an event venue. This geofence experience may provide the user with suggested blends consistent with their usage patterns at specific locations when the user enters a new or existing prior visited location.

Blend database 74 may also provide suggestions based on a user's specific mood. For example, the user could input that they are feeling "low energy" and the blend database could suggest blends that would provide an energy boost. The blend database 74 could include pre-defined moods or a natural language processor that asks the user to input words to describe their mood and while the database decodes an appropriate response and blend for that mood.

Blend database 74 may further include elements of artificial intelligence (AI) or machine learning to learn a user's preferences and make recommendations for existing or new blends. The blend database 74 tracks the user's usage over time, including substances included in cartridges, blends configured (i.e. mixes of various cartridges), GPS location data when particular blends are utilized, time of day/day of week data for blend usage and ratings by the user. With this information, blend database 74 builds a profile of the specific individual user. The system can compare the specific individual user profile with all user profiles in the system (anonymized by removing personally identifiable information) to determine blend recommendations for the user. The system can identify similar usage patterns across users and thus identify favorites across that type of user. Further, the system owner may program various suggested blends based on user profiles that can be recommended, or the system may build its own recommendations based on user profile data. These recommendations may be provided via the application/blend database for consumption options or via the ecommerce functions for product purchases.

Figure 28:
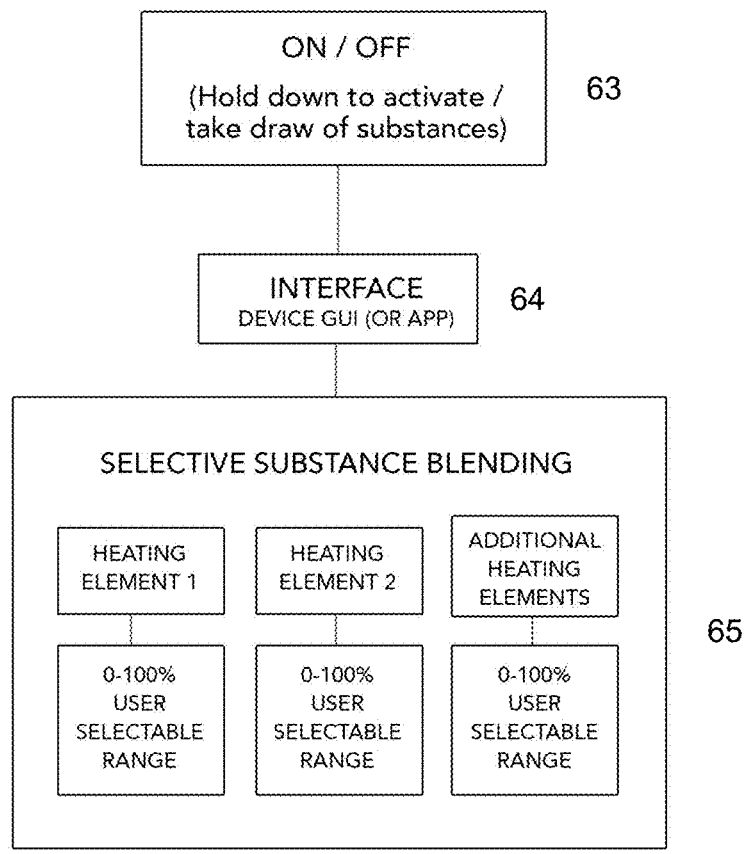
FIG. 28 shows a diagram of the blend ranges.

FIG. 28 is a block diagram of the functionality of one configuration of the preferred embodiment of the multi-element vaporizer system as controlled by a graphical user interface (GUI) on the device or a separate mobile phone application. This diagram shows the available selective substance blending for the device. The user controls selective substance blending using the GUI interface 64 to set the blend of substances desired for vaporization. This GUI interface can be on a display on the actual vaporization device or on a mobile application for an iPhone, Android or other mobile operating system. Selective substance blending 65 allows the user to choose a specific range of blending from 0-100% for each material heated by each heating element. In this example, during a particular user draw cycle, the percentage from 0-100% means the length of time during the draw cycle that heating element is activated. The user may also control the intensity/temperature of the heating element in the GUI controls as part of their selective substance blending but for this simple example the percentage indicates the percent of the total draw cycle where the heating element is activated. Draw cycle means the length of time the user has activated the device with the on/off switch. On/off is indicated in block 63, where holding the on/off button activates the draw cycle where the heating element(s) are activated and the user draws vaporized material through the device.

Figure 29:
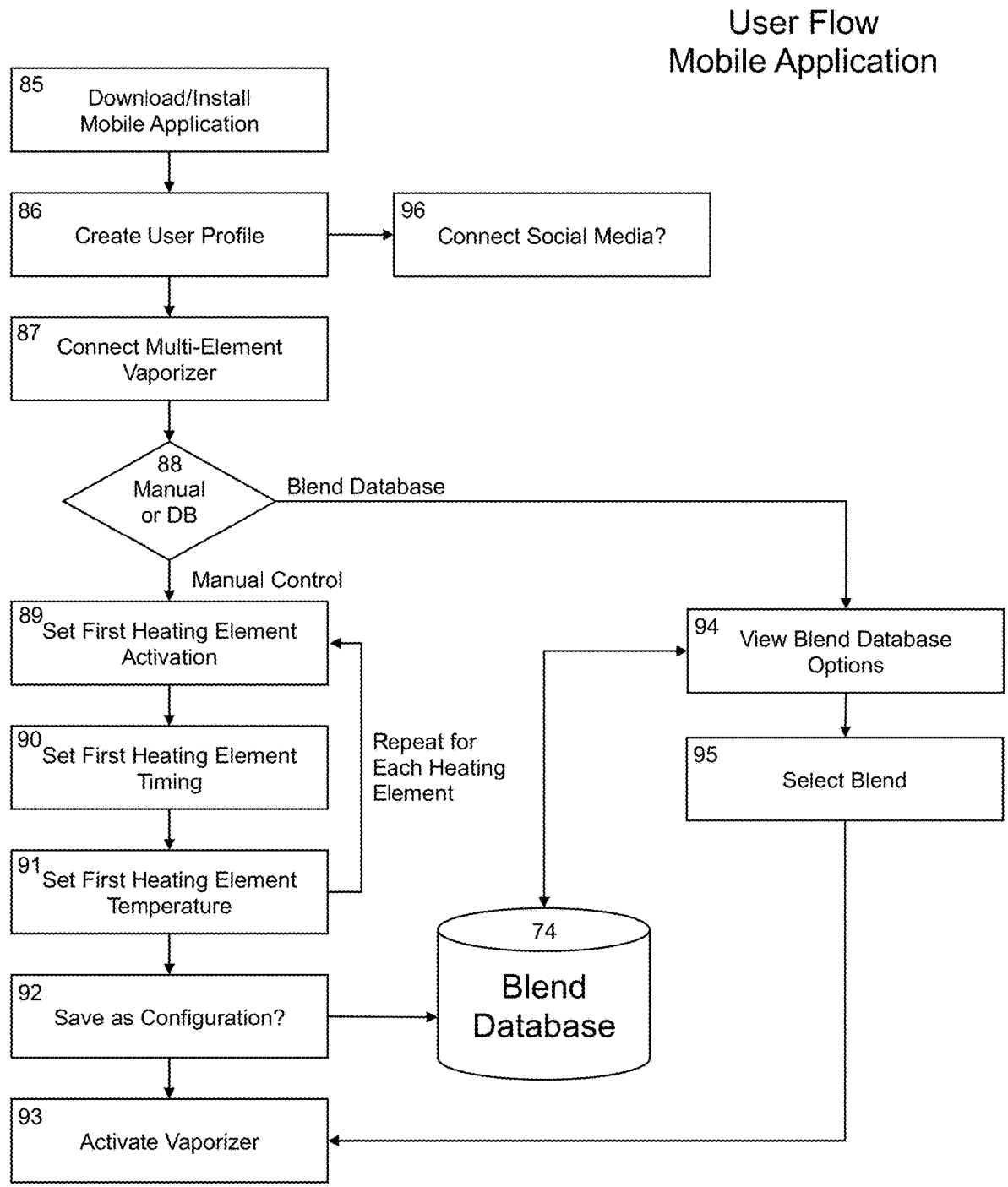
FIG. 29 shows a flow chart of the user flow for the mobile application.

FIG. 29 is a flow chart of the user flow for the multi-element vaporizer utilizing a mobile application to control the device. The first step 85 is for the user to download and install the mobile application. This download is typically done from the App Store for the type of mobile device owned by the user such as the Apple App Store or Google Play Store. Once the application is installed on their mobile device, the user opens the application in step 86 and creates a user profile. This user profile will include at a minimum user name, email address and password. Optionally, the user profile may also include shipping/billing address, credit card information and connection to various social media networks such as Facebook, Twitter and Instagram. The user can optionally connect these social media networks to their user profile in step 96. If the user already has an existing user profile, they have the option of simply logging in rather than creating a new profile. Once the user is logged in to their user profile, the user will connect the multi-element vaporizer device 5 to their mobile device. In the preferred embodiment, this connection is done by Bluetooth pairing after the multi-element vaporizer is placed in pairing mode. Pairing is secure and the connected device can only be used with the paired mobile device and application.

Once the device is paired, or if the user is logged into the app with a paired device, they would start their user flow at step 88 by choosing the configuration of their multi-element vaporizer. There are two configuration options: 1) manual and 2) selecting an existing configuration from the blend database 74. Step 89 starts the manual control path with choosing the first heating element activation. Step 90 allows the user to set the active time for the first heating element. Step 91 allows the user to select the temperature/intensity of the first heating element. In step 92, the user is given the option to share this configuration in blend database 74. The configuration can be saved either as private to only the user or public for other users to select in the blend database 74. The user is given the option to name the blend and provide details about the substances used, configurations and mood effects generated. Once the vaporizer is configured, the user presses the activation button on the multi-element vaporizer and inhales the vaporized material through the air passage.

If the user selects the blend database for configuration, in step 90, the various blend options are presented for user selection. These available blends are organized by (a) type—indica, *sativa* or hybrid, (b) category—flower, oil, concentrate, hash or shatter, (c) strain—name of the particular *Cannabis* strain, (d) characteristics—THC/CBD percentages, and (e) mood effect. The user has the option to select their stored private or public configurations as well. Further the user has the option to search and see blends stored by their social media contacts. The user selects their blend at step 95, then presses the activation button on the multi-element vaporizer and inhales the vaporized material through the air passage.

As described prior, the blend database may provide recommendations based on prior user ratings, user mood, user location, or the user profile built for the user by the AI/machine learning functions.

Figure 30:
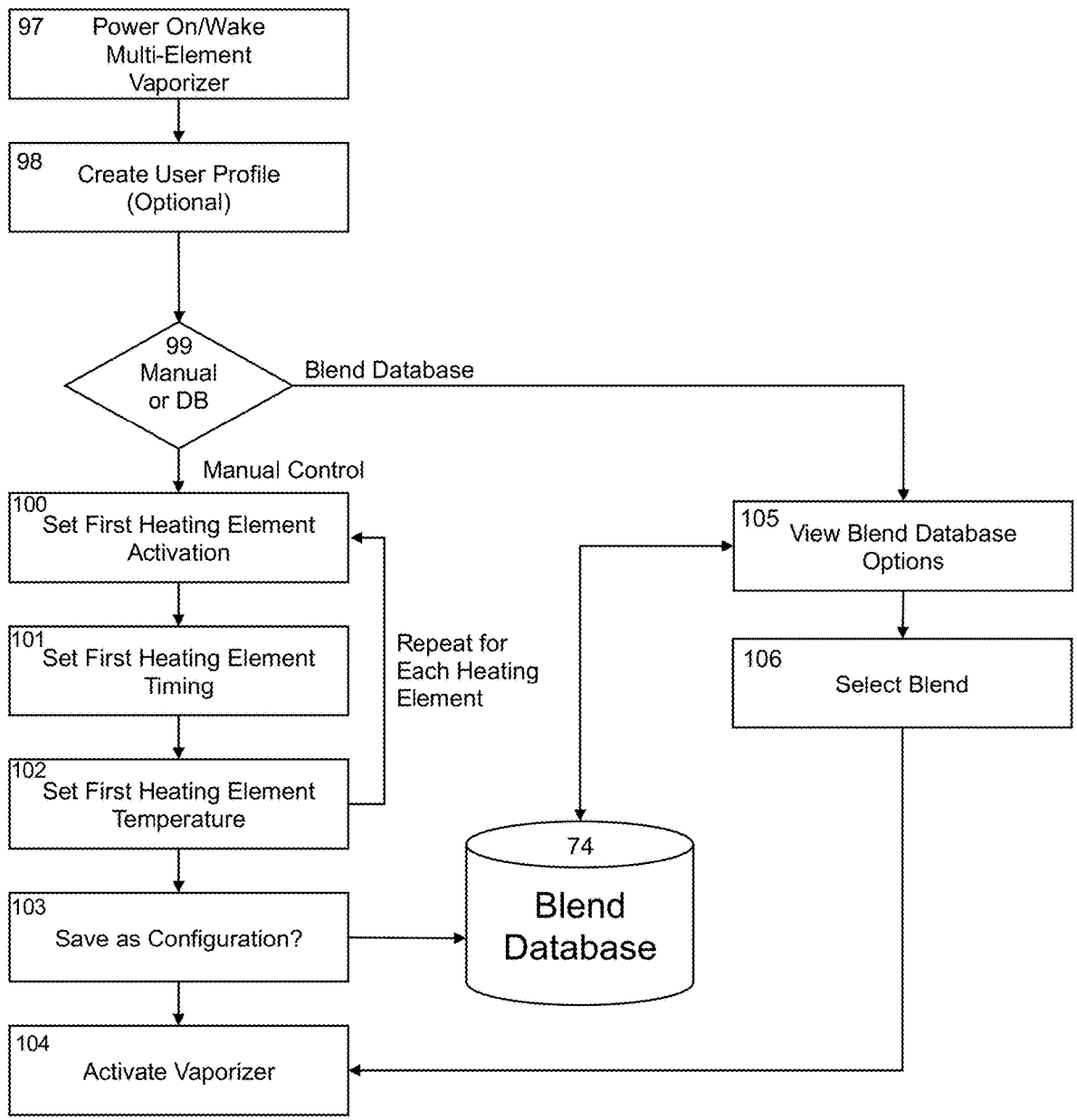
FIG. 30 shows a flow chart of the user flow for the native application.

FIG. 30 is a flow chart of the user flow for the multi-element vaporizer utilizing the native application to control the device. The native application is accessed through an LCD screen implemented on the multi-element vaporizer device. After the device is powered on or woken from a sleep state in step 97, the user is given the option of creating a user profile. This user profile will include a user name, email address and password. If the user already has an existing user profile, they have the option of simply logging in rather than creating a new profile. A user profile is optional however, so the user can jump directly to step 99 to choose manual mode or a blend from the blend database.

Step 100 starts the manual control path with choosing the first heating element activation. Step 101 allows the user to set the active time for the first heating element. Step 102 allows the user to select the temperature/intensity of the first heating element. In step 103, the user is given the option to share this configuration in blend database 74. The configuration can be saved either as private to only the user or public for other users to select in the blend database 74. The user is given the option to name the blend and provide details about the substances used, configurations and mood effects generated. Once the vaporizer is configured, the user presses the activation button on the multi-element vaporizer and inhales the vaporized material through the air passage.

If the user selects the blend database for configuration, in step 99, the various blend options are presented for user selection. These available blends are organized by (a) type—indica, *sativa* or hybrid, (b) category—flower, oil, concentrate, hash or shatter, (c) strain—name of the particular *Cannabis* strain, (d) characteristics—THC/CBD percentages, and (e) mood effect. The user has the option to select their stored private or public configurations as well. Further the user has the option to search and see blends stored by their social media contacts. The user selects their blend at step 95, then presses the activation button on the multi-element vaporizer and inhales the vaporized material through the air passage.

As described prior, the blend database may provide recommendations based on prior user ratings, user mood, user location, or the user profile built for the user by the AI/machine learning functions.

Figure 31:
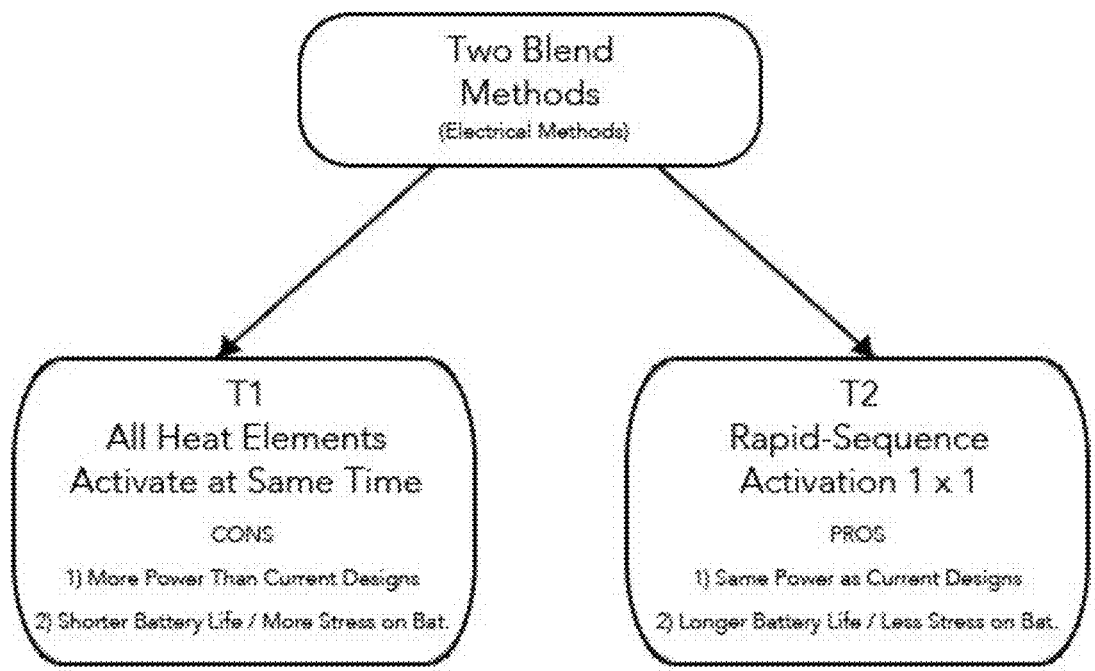
FIG. 31 shows a block diagram of heating methods.

FIG. 31 shows two heating element options for the present device. In the prior art option T1, all the heating elements activate at the same time. This has the disadvantage of increasing the amount of power used by the number of heating elements used in the configuration. For two heating elements, the power consumption would be double, for three it would be triple and so on. The present invention uses a method that rapidly cycles the heating elements in a sequence. The heating elements stay hot but only one is actively powered at a given time. To the user, it appears that the output is the same, but the power consumption is the same as a single heating element design.

The present figures and detailed description disclose the preferred embodiment of the claimed invention and are not meant to limit the scope of the claims. Many other configurations and embodiments are possible within the scope of the present claims.

The invention claimed is:

1. A system for vaporizing smokable materials for personal inhalation by a user comprising:
    a portable vaporizer device comprising:
        two or more heating elements, each heating element disposed to apply heat to an individual smokable material to vaporize the material and being individually controlled for activation and temperature;
        a power source;
        a switching element that controls the activation, duration of activation and temperature of each heating element individually;
        a wireless communication means to operatively connect the portable vaporizer device to a computer application installed on a computer system;
        at least one control for activating the portable vaporizer device;
    a computer application installed on a computer system, said computer system including a wireless communication means to operatively communicate with the portable vaporizer device and a connection to the internet, said computer application comprising:
        a user interface for controlling the computer application;
        a user profile for the user;
        ecommerce functions allowing the user to purchase related products from
        an online store;
        settings for each heating element on the portable vaporizer device that allow the user to individually control the activation, duration of activation and temperature of each heating element, the application being configured to save the settings as a device configuration profile with the user profile;
        a blend database for saving multiple device configuration profiles; and
        a user calendar where user device configuration profiles can be saved by date and time of day and activated by date and time of day by the user.

2. The system for vaporizing smokable materials for personal inhalation by a user of claim 1 where the blend database further comprises a rating system where a user may input a rating of a user device configuration profile.

3. The system for vaporizing smokable materials for personal inhalation by a user of claim 1 where the blend database further comprises suggested device configuration profiles based on an input by the user.

4. The system for vaporizing smokable materials for personal inhalation by a user of claim 1 where the blend database further comprises suggested device configuration profiles based on user location.

5. The system for vaporizing smokable materials for personal inhalation by a user of claim 1 where the computer application further comprises authorizing a social connection via a social network and a notification system for notifying the user of activity of an authorized social connection.

6. The system for vaporizing smokable materials for personal inhalation by a user of claim 1 where each heating element is contained within a cavity also containing the smokable material.

7. The system for vaporizing smokable materials for personal inhalation by a user of claim 6 where the cavity is attachable and detachable to the portable vaporizer with screw type threads.

8. The system for vaporizing smokable materials for personal inhalation by a user of claim 6 where the cavity is attachable and detachable to the portable vaporizer by a plug-in type connector.

9. The system for vaporizing smokable materials for personal inhalation by a user of claim 6 where the cavity is attachable and detachable to the portable vaporizer by a magnetic connector.

10. The system for vaporizing smokable materials for personal inhalation by a user of claim 6 where the cavity has a removable cap.

11. The system for vaporizing smokable materials for personal inhalation by a user of claim 1 where the smokable material is fluid, oil, juice, wax, dab, shatter, distillate, flower, hash, tobacco or plant matter.

12. A system for vaporizing smokable materials for personal inhalation by a user comprising:
    two or more heating elements, each heating element disposed to apply heat to an individual smokable material to vaporize the material and being individually controlled for activation and temperature;
    a power source;
    a switching element that controls the activation, duration of activation and temperature of each heating element individually;
    at least one control for activating the portable vaporizer device;
    a vaporizer control system comprising:
        a microprocessor;
        memory for storing an application for controlling the vaporizer system;
        a touch sensitive display for displaying the application, the touch sensitive display controlled by a touch sensitive display controller;
        a wireless communication module that allows the system to operatively connect to another computer system and the internet;
    the application comprising:
        a user interface for controlling the application;
        settings for each heating element of the vaporizer system that allows the user to individually control the activation, duration of activation and temperature of each heating element, the application being configured to save the settings as a device configuration profile;
        a blend database of multiple device configuration profiles; and
        a user calendar where user device configuration profiles can be saved by date and time of day and activated by date and time of day by the user.

13. The system for vaporizing smokable materials for personal inhalation by a user of claim 12 where the blend database further comprises a rating system where a user may input a rating of a user device configuration profile.

14. The system for vaporizing smokable materials for personal inhalation by a user of claim 12 where the blend database further comprises suggested device configuration profiles based on an input by the user.

15. The system for vaporizing smokable materials for personal inhalation by a user of claim 12 where the blend database further comprises suggested device configuration profiles based on user location.

16. The system for vaporizing smokable materials for personal inhalation by a user of claim 1 where the computer application further comprises authorizing a social connection via a social network and a notification system for notifying the user of activity of an authorized social connection.

17. The system for vaporizing smokable materials for personal inhalation by a user of claim 12 where each heating element is contained within a cavity also containing the smokable material.

18. The system for vaporizing smokable materials for personal inhalation by a user of claim 17 where the cavity is attachable and detachable to the portable vaporizer with screw type threads.

19. The system for vaporizing smokable materials for personal inhalation by a user of claim 17 where the cavity is attachable and detachable to the portable vaporizer by a plug-in type connector.

20. The system for vaporizing smokable materials for personal inhalation by a user of claim 17 where the cavity has a removable cap.

* * * * *